(12) United States Patent
Gupta et al.

(10) Patent No.: US 11,312,043 B2
(45) Date of Patent: Apr. 26, 2022

(54) PROCESSING ADDITIVES AND USES OF SAME IN ROTATIONAL MOLDING

(75) Inventors: Ram Gupta, Stamford, CT (US); Sari-Beth Samuels, Ramsey, NJ (US); Thomas Steele, Milford, CT (US); J. Mon Hei Eng, Wilton, CT (US)

(73) Assignee: CYTEC TECHNOLOGY CORP., Princeton, NJ (US)

( * ) Notice: Subject to any disclaimer, the term of this patent is extended or adjusted under 35 U.S.C. 154(b) by 141 days.

(21) Appl. No.: 13/323,173

(22) Filed: Dec. 12, 2011

(65) Prior Publication Data

US 2012/0146257 A1 Jun. 14, 2012

Related U.S. Application Data

(60) Provisional application No. 61/422,255, filed on Dec. 13, 2010.

(51) Int. Cl.
| | | |
|---|---|---|
| *C08K 5/00* | (2006.01) | |
| *B29C 41/04* | (2006.01) | |
| *C07D 311/72* | (2006.01) | |
| *C08K 5/34* | (2006.01) | |
| *C08K 5/1545* | (2006.01) | |
| *C08L 23/08* | (2006.01) | |
| *C08K 5/51* | (2006.01) | |
| *B29K 23/00* | (2006.01) | |

(52) U.S. Cl.
CPC ............ *B29C 41/04* (2013.01); *C07D 311/72* (2013.01); *C08K 5/00* (2013.01); *C08K 5/005* (2013.01); *C08K 5/1545* (2013.01); *C08K 5/34* (2013.01); *C08K 5/51* (2013.01); *C08L 23/0815* (2013.01); *B29K 2023/0625* (2013.01); *Y02P 20/10* (2015.11)

(58) Field of Classification Search
CPC .................. C08K 5/005; C07D 311/72; B29K 2023/0625; B29C 41/04
USPC ................................................. 264/310, 311
See application file for complete search history.

(56) References Cited

U.S. PATENT DOCUMENTS

| | | |
|---|---|---|
| 4,240,961 A | 12/1980 | Lai |
| 4,325,863 A | 4/1982 | Hinsken et al. |
| 4,338,244 A | 7/1982 | Hinsken et al. |
| 4,480,092 A | 10/1984 | Lai et al. |
| 4,489,099 A | 12/1984 | Shaheen et al. |
| 4,629,752 A | 12/1986 | Layer et al. |
| 4,639,479 A | 1/1987 | Lai et al. |
| 4,694,090 A | 9/1987 | Shiono et al. |
| 4,806,580 A | 2/1989 | Bock et al. |
| 4,925,888 A | 5/1990 | Aumueller et al. |
| 5,013,836 A | 5/1991 | Lai |
| 5,175,312 A | 12/1992 | Dubs et al. |
| 5,216,052 A | 6/1993 | Nesvadba et al. |
| 5,218,008 A | 6/1993 | Parrish |
| 5,252,643 A | 10/1993 | Nesvadba |
| 5,262,471 A * | 11/1993 | Akao ........................ C08J 3/226 524/487 |
| 5,308,549 A | 5/1994 | Laermer et al. |
| 5,310,771 A | 5/1994 | Walters |
| 5,356,966 A | 10/1994 | Nesvadba |
| 5,357,020 A * | 10/1994 | Cogen et al. ................... 528/27 |
| 5,367,008 A | 11/1994 | Nesvadba |
| 5,369,159 A | 11/1994 | Nesvadba |
| 5,426,141 A | 6/1995 | Akao |
| 5,428,162 A | 6/1995 | Nesvadba |
| 5,428,177 A | 6/1995 | Nesvadba |
| 5,488,117 A | 1/1996 | Nesvadba |
| 5,516,920 A | 5/1996 | Nesvadba et al. |
| H1600 H * | 10/1996 | Imfeld .......................... 524/100 |
| 5,594,055 A | 1/1997 | Young |
| 5,747,568 A | 5/1998 | Fischer et al. |
| 5,807,504 A | 9/1998 | Krockenberger et al. |
| 5,837,759 A | 11/1998 | Trauth et al. |
| 5,844,027 A | 12/1998 | Burdick et al. |

(Continued)

FOREIGN PATENT DOCUMENTS

| | | |
|---|---|---|
| CA | 1241009 A | 8/1988 |
| EP | 0682073 A2 | 11/1995 |

(Continued)

OTHER PUBLICATIONS

"Metallocene Polyethylene Films." Brentwood Plastics, Retrieved from https://www.brentwoodplastics.com/metallocene on Dec. 14, 2020. (Year: 2020).*
International Search Report for PCT/US2011/064320; dated Jun. 8, 2012.
Written Opinion for PCT/US2011/064320; dated Jun. 8, 2012.
Laermer and Zambetti, "Alpha-Tocopherol (Vitamin E)—the Natural Antioxidant for Polyolefins;" Journal of Plastic Film and Sheeting; 1992; V-8; pp. 228-248.

(Continued)

*Primary Examiner* — Atul P. Khare
(74) *Attorney, Agent, or Firm* — Dennis J. Jakiela; Charles E. Bell, Esq.

(57) ABSTRACT

The cycle time of polymer compositions subjected to a rotomolding process is improved (i.e., reduced), while the processing window is simultaneously enlarged through the use of a polymer-stabilizing amount of a processing stabilizer system having at least one chroman-based compound according to Formula V:

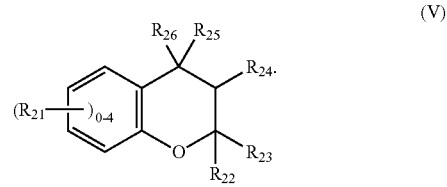

(V)

8 Claims, 3 Drawing Sheets

(56) References Cited

U.S. PATENT DOCUMENTS

| | | | |
|---|---|---|---|
| 5,877,242 A * | 3/1999 | Niessner | C08K 5/1545 524/111 |
| 5,883,165 A | 3/1999 | Krohnke et al. | |
| 6,022,915 A | 2/2000 | Ticktin et al. | |
| 6,051,164 A * | 4/2000 | Samuels | 252/404 |
| 6,056,897 A | 5/2000 | Pallini et al. | |
| 6,271,377 B1 | 8/2001 | Galbo et al. | |
| 6,444,733 B1 | 9/2002 | Stadler | |
| 6,465,548 B1 | 10/2002 | Inoue et al. | |
| 6,468,258 B1 | 10/2002 | Shang | |
| 6,492,442 B1 | 12/2002 | Appel et al. | |
| 6,541,547 B1 | 4/2003 | Schmutz et al. | |
| 6,689,838 B1 * | 2/2004 | Fischer | C08L 67/02 525/230 |
| 6,843,939 B2 | 1/2005 | Stretanski et al. | |
| 6,902,695 B2 | 6/2005 | Stadler | |
| 7,109,259 B2 | 9/2006 | Lazzari et al. | |
| 7,144,919 B1 | 12/2006 | Kim et al. | |
| 7,307,126 B2 | 12/2007 | Lustiger et al. | |
| 7,375,149 B2 * | 5/2008 | Rotzinger et al. | 524/110 |
| 7,479,515 B2 * | 1/2009 | Schmidt | C08L 23/10 524/210 |
| 8,044,161 B2 | 10/2011 | Tiitinen et al. | |
| 2004/0210056 A1 * | 10/2004 | Wood | C07D 211/94 546/216 |
| 2005/0004275 A1 | 1/2005 | Heidenfelder et al. | |
| 2006/0167146 A1 | 7/2006 | Rotzinger et al. | |
| 2007/0227087 A1 * | 10/2007 | Nasr | B44C 5/0453 52/314 |
| 2007/0256352 A1 * | 11/2007 | Wood | C07B 63/04 44/275 |
| 2009/0085252 A1 * | 4/2009 | Minder et al. | 264/310 |
| 2010/0266798 A1 | 10/2010 | Anker et al. | |
| 2010/0327487 A1 | 12/2010 | Yu et al. | |
| 2011/0272648 A1 | 11/2011 | Fukushima et al. | |
| 2013/0145962 A1 | 6/2013 | Gupta et al. | |

FOREIGN PATENT DOCUMENTS

| | | | | |
|---|---|---|---|---|
| EP | 0889085 B1 | 7/2002 | | |
| EP | 1308084 A1 | 5/2003 | | |
| EP | 2014704 B1 | 12/2010 | | |
| GB | 2260764 A * | 4/1993 | | C08K 5/1545 |
| JP | 5455043 A | 5/1979 | | |
| JP | 58096638 A * | 6/1983 | | |
| JP | S5896638 A | 6/1983 | | |
| JP | 01170632 A * | 7/1989 | | |
| JP | H01170632 | 7/1989 | | |
| JP | H0335552 A | 2/1991 | | |
| JP | 2001212837 A * | 8/2001 | | |
| JP | 2001212837 A * | 8/2001 | | |
| JP | 2011153251 A | 8/2011 | | |
| WO | 198808863 A1 | 11/1988 | | |
| WO | 9007547 A1 | 7/1990 | | |
| WO | 199007547 A1 | 7/1990 | | |
| WO | WO-9519391 A1 * | 7/1995 | | C08K 5/005 |
| WO | 1997003974 A2 | 2/1997 | | |
| WO | 1997049758 A1 | 12/1997 | | |
| WO | WO-9948997 A1 * | 9/1999 | | C08K 5/524 |
| WO | 2004024810 A2 | 3/2004 | | |
| WO | 2007088130 A1 | 8/2007 | | |
| WO | 2007104689 A1 | 9/2007 | | |
| WO | 2008124825 A2 | 10/2008 | | |
| WO | 2009007265 A1 | 1/2009 | | |
| WO | 2013188490 A1 | 12/2013 | | |

OTHER PUBLICATIONS

James H. Botkin et al., "An Additive Approach to Cycle Time Reduction in Rotational Molding;" Society of Plastics Engineers, Rotomolding Conference, Session 2, 2004.
International Search Report for PCT/US2013/045318; dated Aug. 7, 2013.
International Preliminary Report on Patentability for PCT/US2013/045318; dated Dec. 24, 2014.
Huang et al "Comparison of free radical formation induced by baicalein and pentamethyl-hydroxychromane in human promyelocytic leukemia cells using electron spin resource"; Journal of Food and Drug Analysis 22; 2014; pp. 379-390.
Machine Translation for JP2011153251.
Office Action dated Apr. 4, 2016 for U.S. Appl. No. 13/495,109.
Office Action dated Dec. 9, 2016 For U.S. Appl. No. 13/495,109.
Office Action dated Aug. 24, 2017 for U.S. Appl. No. 13/495,109.
Partial Translation for JPH01170632.
Partial Translation for JPS58096638.
Chap. 3, 'PVC Stabilizers and Plasticizers', In Zweifel, Maier, Schiller, Ed. 'Plastics Additives Handbook', 6th Ed, pp. 425-433.
Van Henegouwen et al., J. Photochem. and Photobio, 29, 1995, pp. 45-51.
Office Action dated Apr. 14, 2021 for U.S. Appl. No. 13/495,109.

\* cited by examiner

PROCESSING ADDITIVES AND USES OF SAME IN ROTATIONAL MOLDING

CROSS-REFERENCE TO RELATED APPLICATIONS

This application claims benefit of priority to U.S. Provisional Application No. 61/422,255 filed Dec. 13, 2010 the content of which is incorporated herein by reference in its entirety.

This application is also the parent application of a continuation-in-part application, U.S. application Ser. No. 13/495,109, filed Jun. 13, 2012 (pending).

BACKGROUND OF THE INVENTION

1. Field of the Invention

The present invention generally relates to the production of hollow articles using the rotational molding process. More particularly, the present invention relates to the additives described hereinbelow and their use in such processes to improve molding cycle time (i.e., reducing curing time) while maintaining process stability over a broader range of temperatures.

2. Description of the Related Art

Rotational molding, or rotomolding, is a high-temperature, low-pressure forming process that uses heat and biaxial rotation to produce hollow, one-piece parts, typically made of plastic. Such plastic hollow parts typically made by a rotomolding process include, for example, gasoline containers, garbage cans, agricultural storage vessels, septic tanks, toys, and sporting goods such as kayaks.

The process is undertaken by loading a charge of finely divided plastic resin into the mold "shell", then rotating the mold (usually, on two axes) while heating it to a temperature above the melting point of the plastic resin. The melted plastic flows through the mold cavity under the forces caused by the rotation of the apparatus. The rotation continues for sufficient time to allow the molten plastic to cover the surface of the mold. The mold is then cooled to permit the plastic to freeze into a solid. The final stage of the molding cycle is the removal of the part from the rotomolding machine.

The time required to complete the molding cycle is a function of the bulk properties of the plastic which is being molded. For example, it is recognized by those skilled in the art that the plastic resin which is charged into the mold is preferably finely divided (i.e. ground into powder) and has a high bulk density and a narrow particle size distribution to facilitate the "free flow" of the resin.

It will also be appreciated that the physical properties of the rotomolded part are influenced by the use of a proper molding cycle time with "undercooked" parts having poor strength properties and "overcooked" parts suffering from poor appearance (a "burnt" color) and/or a deterioration of strength properties. It is desirable to have a short molding cycle (so as to improve the productivity of the expensive rotomolding machinery) and a broad processing window. Thus, the rotomolding composition ideally provides "properly cooked" parts in a short period of time but does not become "overcooked" for an extended period of time.

Therefore, the length of time the resin-filled mold spends in the oven is critical, because if left too long the polymer will yellow and/or degrade, thereby negatively affecting the mechanical and/or physical properties of the molded article (e.g., reducing impact strength). If the time the resin filled mold spends in the oven is too short, the scintering and laydown of the molten polymer will be incomplete, thereby negatively affecting the final physical and/or mechanical properties of the molded article. Thus, there is only a narrow temperature and/or time range for achieving the desired mechanical and/or physical properties of the molded article (i.e., processing window). Accordingly, it would be advantageous to widen/broaden this processing window so that parts that have been processed with longer oven cycle times will still exhibit optimal mechanical and/or physical properties.

Various additives are known and have been used in the rotomolding process to stabilize the polyolefin material and effectively reduce the production of microstructural defects during the heating cycle of the rotomolding process, which negatively affect the molded article. Some of these additives are also known to affect the cycle time of the rotomolding process. See, e.g., Botkin et al., 2004 "An additive approach to cycle time reduction in rotational molding," Society of Plastics Engineers Rotomolding Conference, Session 2. For example, the use of stabilizer combinations of phosphites or phosphonites with sterically hindered phenols in polyolefins is generally known. Such phenolic/phosphite or phosphonite blends (e.g., CYANOX® 2777 antioxidant (available from Cytec Industries Inc., Woodland Park N.J.)) will stabilize the resin in the oven for a longer time (resulting in a broader process window), but requires a longer time in the oven to achieve maximum physical properties (resulting in a longer cycle time). Other stabilizer compositions (e.g., hydroxylamine derivatives blended with phosphites and/or phosphonites and HALS), allow for faster polymerization and cure times of the resins, but the processing window remains very narrow. For example, improvements to widen the processing window by using sterically hindered amines are disclosed in US Publication No. 2009/0085252.

Accordingly, the rotational molding of polyolefin resins requires further improvements in cycle time reduction. A stabilizer composition that effectively reduces the time for scintering and laydown of the polymer melt (with reduced oven cycle time), while maintaining a broad processing window, would be a useful advance in the field, and would find rapid acceptance in the rotational molding industry. Shorter cycle times would lead to greater production yield, higher production efficiency, and, thus, lower energy uses. Formulations exhibiting a broadened process window would be easier to fabricate, without concerns about overcuring and the potential for deterioration of the mechanical properties of the resulting part. Further, formulations exhibiting both a broadened process window and shorter cycle time would enable molders to fabricate parts of different thickness at the same time, thereby further enhancing productivity.

SUMMARY OF THE INVENTION

The discovery described in detail hereinbelow provides stabilizer compositions and processes for using same for reducing cycle time without compromising the processing window in rotational molding processes related to polyolefin articles. These stabilizer compositions and processes effectively reduce the time in the oven needed to reach optimal physical and/or mechanical properties, thereby reducing cycle times of the rotomolding process and consequently increasing production yield and production efficiency, and lowering energy requirements.

Accordingly, in one aspect the invention provides a process for reducing cycle time and/or maintaining a broad process window in a rotational molding process for producing a polymeric hollow article, by subjecting a polymer composition and a polymer-stabilizing amount of a stabilizer composition to a rotational molding process, wherein the stabilizer composition includes:

i) at least one chroman-based compound according to Formula V

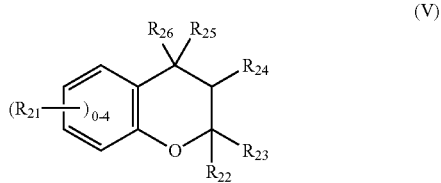

wherein $R_{21}$ is present at from 0 to 4 positions of the aromatic portion of Formula V and in each position is independently chosen from:

$C_1$-$C_{12}$ hydrocarbyl;

NR'R", wherein each of R' and R" is independently chosen from H or $C_1$-$C_{12}$ hydrocarbyl; or $OR_{27}$, wherein $R_{27}$ is chosen from: H; $C_1$-$C_{12}$ hydrocarbyl; COR'''; or Si($R_{28}$)$_3$, wherein R''' is chosen from H or $C_1$-$C_{20}$ hydrocarbyl; and wherein $R_{28}$ is chosen from $C_1$-$C_{12}$ hydrocarbyl or alkoxy;

$R_{22}$ is chosen from: H; or $C_1$-$C_{12}$ hydrocarbyl;

$R_{23}$ is chosen from H; or $C_1$-$C_{20}$ hydrocarbyl;

each of $R_{24}$-$R_{25}$ is independently chosen from: H; $C_1$-$C_{12}$ hydrocarbyl; or OR'''', wherein R'''' is chosen from H or $C_1$-$C_{12}$ hydrocarbyl; and $R_{26}$ is H, or a bond which together with $R_{25}$ forms =O.

In another aspect, the invention provides processes for producing a polymeric hollow article, by a) filling a mold with a polymer composition and a polymer-stabilizing amount of a stabilizer composition including at least one chroman-based compound according to Formula V (as described above), b) rotating the mold around at least 1 axis while heating the mold in an oven, thereby fusing the composition and spreading it to the walls of the mold; c) cooling the mold; and d) opening the mold to remove the resulting product, thereby producing a polymeric hollow article.

In another aspect, the invention provides a stabilizer composition having:

a) at least one compound chosen from the group of organic phosphites and phosphonites;

b) at least one hindered phenol compound; and c) from 0.001% to 5% by weight of the total of at least one chroman-based compound according to Formula V (as described above).

In another aspect, the invention provides a stabilizer composition consisting of a) at least one compound chosen from the group of organic phosphites and phosphonites;

b) at least one hindered phenol compound; and c) at least one chroman-based compound according to Formula V (as described above).

In still other aspects, the invention provides kits for stabilizing a polyolefin composition for use in a rotomolding process including in one or more containers a polymer-stabilizing amount of a stabilizer composition as described herein, as well as provides rotomolded articles that are produced according to the processes described herein, or that contain a stabilizer composition as described herein.

These and other objects, features and advantages of this invention will become apparent from the following detailed description of the various aspects of the invention taken in conjunction with the accompanying Figures and Examples.

DETAILED DESCRIPTION OF CERTAIN EMBODIMENTS OF THE INVENTION

Figure 1:
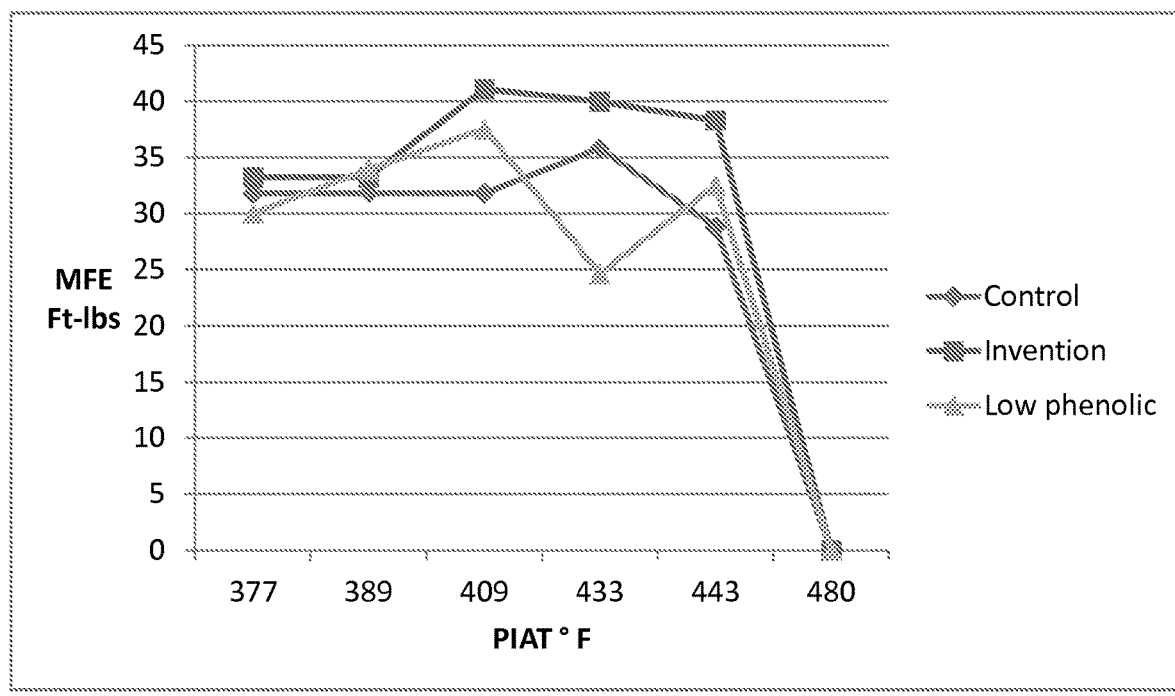
FIG. 1 illustrates the mean failure energy (MFE) of rotomolded parts made with control stabilizer system (♦) vs. low phenolic stabilizer system (▲) vs. a processing stabilizer system according to the invention (■). As seen, the rotomolded part that was formulated with the stabilizer system according to the invention (■) achieves the highest MFE (as determined by the Dart Drop Low Temperature Impact Resistance Test Procedure) at a shorter rotational molding time interval (given by peak internal air temperature) compared to the rotomolded part that was formulated with either the control stabilizer system (♦) or the low phenolic stabilizer system (▲). Furthermore, the rotomolded part formulated according to the invention unexpectedly retains a higher MFE at longer oven times than do the rotomolded parts formulated with either the control or low phenolic stabilizer systems. Accordingly, the benefit of using a processing stabilizer according to the invention in a rotational molding process is due to the use of a chroman-based compound and not due to use of a lower amount of phenolic/phosphite.

As summarized above, the compositions and processes using same that have now been discovered and disclosed herein for the first time are surprisingly useful for achieving optimal physical and/or mechanical properties of a rotomolded hollow article in a shorter period of time in the oven (i.e., cycle time) compared to those rotomolded articles made with current commercially available polymer stabilizer packages. Furthermore, the processes and compositions disclosed herein additionally (and surprisingly) provide a wider/broader processing window within which the desired final properties of the rotomolded article can be obtained before the physical and/or mechanical properties are negatively affected.

Definitions

As employed above and throughout the disclosure, the following terms are provided to assist the reader. Unless otherwise defined, all terms of art, notations and other scientific terminology used herein are intended to have the meanings commonly understood by those of skill in the chemical arts. As used herein and in the appended claims, the singular forms include plural referents unless the context clearly dictates otherwise.

Throughout this specification the terms and substituents retain their definitions. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

The term "hydrocarbyl" is a generic term encompassing aliphatic, alicyclic and aromatic groups having an all-carbon backbone and consisting of carbon and hydrogen atoms. In certain cases, as defined herein, one or more of the carbon atoms making up the carbon backbone may be replaced or interrupted by a specified atom or group of atoms, such as by one or more heteroatom of N, O, and/or S. Examples of hydrocarbyl groups include alkyl, cycloalkyl, cycloalkenyl, carbocyclic aryl, alkenyl, alkynyl, alkylcycloalkyl, cycloalkylalkyl, cycloalkenylalkyl, and carbocyclic aralkyl, alkaryl, aralkenyl and aralkynyl groups. Such hydrocarbyl groups can also be optionally substituted by one or more substituents as defined herein. Accordingly, the chemical groups or moieties discussed in the specification and claims should be understood to include the substituted or unsubstituted forms. The examples and preferences expressed below also apply to each of the hydrocarbyl substituent groups or hydrocarbyl-containing substituent groups referred to in the various definitions of substituents for compounds of the formulas described herein unless the context indicates otherwise.

Preferred non-aromatic hydrocarbyl groups are saturated groups such as alkyl and cycloalkyl groups. Generally, and by way of example, the hydrocarbyl groups can have up to fifty carbon atoms, unless the context requires otherwise. Hydrocarbyl groups with from 1 to 30 carbon atoms are preferred. Within the sub-set of hydrocarbyl groups having 1 to 30 carbon atoms, particular examples are $C_{1-20}$ hydrocarbyl groups, such as $C_{1-12}$ hydrocarbyl groups (e.g. $C_{1-6}$ hydrocarbyl groups or $C_{1-4}$ hydrocarbyl groups), specific examples being any individual value or combination of values selected from $C_1$ through C30 hydrocarbyl groups.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{30}$ or below.

Alkoxy or alkoxyalkyl refers to groups of from 1 to 20 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like.

Acyl refers to formyl and to groups of 1, 2, 3, 4, 5, 6, 7, 8, 9, 10, 11 and 12 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl, t-butoxycarbonyl, benzyloxycarbonyl and the like. Lower-acyl refers to groups containing one to six carbons.

References to "carbocyclic" or "cycloalkyl" groups as used herein shall, unless the context indicates otherwise, include both aromatic and non-aromatic ring systems. Thus, for example, the term includes within its scope aromatic, non-aromatic, unsaturated, partially saturated and fully saturated carbocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members. Examples of non-aromatic carbocycle/cycloalkyl groups include c-propyl, c-butyl, c-pentyl, c-hexyl, and the like. Examples of $C_7$ to $C_{10}$ polycyclic hydrocarbons include ring systems such as norbornyl and adamantyl.

Aryl (carbocyclic aryl) refers to a 5- or 6-membered aromatic carbocycle ring containing; a bicyclic 9- or 10-membered aromatic ring system; or a tricyclic 13- or 14-membered aromatic ring system. The aromatic 6- to 14-membered carbocyclic rings include, e.g., substituted or unsubstituted phenyl groups, benzene, naphthalene, indane, tetralin, and fluorene.

Substituted hydrocarbyl, alkyl, aryl, cycloalkyl, alkoxy, etc. refer to the specific substituent wherein up to three H atoms in each residue are replaced with alkyl, halogen, haloalkyl, hydroxy, alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, halobenzyl, heteroaryl, phenoxy, benzyloxy, heteroaryloxy, benzoyl, halobenzoyl, or lower alkylhydroxy.

The term "halogen" means fluorine, chlorine, bromine or iodine.

As used herein, the term "chroman-based compound" refers to those compounds having a functional chroman group as part of the compound. In certain embodiments the chroman-based compound will be substituted. In other embodiments, the chroman-based compound can include chromanones. Coumarin and tocotrienols are specific examples of chroman-based compounds.

The terms "cycle time" or "molding cycle" as used herein are given their ordinary meaning as commonly understood by those of skill in the rotomolding arts and refer to the time from one point in the cycle to the corresponding point in the next repeated sequence (i.e., the time required to produce a plastic part in a molding operation as measured from a point of one operation to the same point of the first repeat of the operation).

The terms "optimal mechanical property" or "optimal physical property" as used herein refer to rotomolded parts having the most desirable: impact strength, coalescence or sintering of polymer particles, and general appearance such as color.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Processes

Rotational molding technology is well known and described in the literature. Many aspects of the rotational molding process are described, for example, by R. J. Crawford and J. L. Throne in *Rotational Molding Technology*, Plastics Design Library, William Andrew Publishing, 2001. The rotomolded articles described herein are made from stabilized polymer compositions according to the invention using rotational molding techniques generally accepted by those skilled in the art as being representative of commercial rotational molding processes. In general, these rotational molding techniques involve the use of a rotational mold and an oven. A polymer composition (e.g., a stabilized polymer composition including a stabilizer composition and a polymer composition as described herein) is placed in a mold possessing a predetermined shape. The mold is heated within the oven at a predetermined rate to a peak temperature. During heating, the resin melts and the mold is rotated in two or three dimensions to ensure that the melted resin evenly coats the interior surfaces of the mold. Optionally, the melted resin may be cured for a predetermined time. After heating is complete, the mold is removed from the oven and cooled (with the mold optionally being in rotation). Once cool, the formed plastic part is removed from the mold.

Surprisingly, it has now been found that when at least one chroman-based compound is added to the rotomolding resin formulation the time at which it takes to reach peak internal air temperature (PIAT) is reduced and a significantly broader processing window towards higher temperatures is achieved without adversely affecting the physical and/or mechanical properties of the molded article.

Consequently, in one aspect the invention provides a process for reducing cycle time while maintaining an enlarged process window in a rotational molding process for producing a polymeric hollow article by subjecting a polymer composition and a polymer-stabilizing amount of a stabilizer composition to a rotational molding process, wherein the stabilizer composition includes at least one chroman-based compound according to Formula V as described herein.

In certain embodiments, the cycle time of the process will be reduced by at least 4%, at least 5%, at least 10%, at least 15%, or at least 20%, at least 25%, at least 40%, or at least 50% as compared to a process that does not include at least one chroman-based compound in the resin formulation.

In another aspect, the invention provides a process for producing a polymeric hollow article by a) filling a mold with a polymer composition and a polymer-stabilizing amount of a stabilizer composition, wherein the stabilizer composition includes at least one chroman-based compound according to Formula V as described herein; b) rotating the mold around at least one axis while heating the mold in an oven, thereby fusing the composition and spreading it to the walls of the mold; c) cooling the mold; and d) opening the mold to remove the resulting product, thereby producing a polymeric hollow article.

During the rotomolding process, the temperature of the oven can reach from 70° C. to 400° C., preferably from 280° C. to 400° C., and more preferably from 310° C. to 400° C.

The stabilized polymer compositions suitable for use with the aforementioned processes are further described below.

Stabilized Polymer Compositions

The stabilizer compositions according to the invention and suitable for use with the polymer compositions for the rotomolding processes as described herein include at least one chroman-based compound according to Formula V:

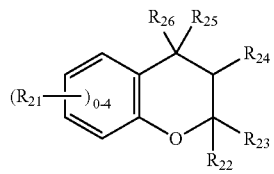

wherein $R_{21}$ is present at from 0 to 4 positions of the aromatic portion of Formula V and in each instance is independently chosen from:

$C_1$-$C_{12}$ hydrocarbyl;

NR'R", wherein each of R' and R" is independently chosen from H or $C_1$-$C_{12}$ hydrocarbyl; or $OR_{27}$, wherein $R_{27}$ is chosen from: H; $C_1$-$C_{12}$ hydrocarbyl; COR'''; or Si($R_{28}$)$_3$, wherein R''' is chosen from H or $C_1$-$C_{20}$ hydrocarbyl; and wherein $R_{28}$ is chosen from $C_1$-$C_{12}$ hydrocarbyl or alkoxy;

$R_{22}$ is chosen from: H; or $C_1$-$C_{12}$ hydrocarbyl;

$R_{23}$ is chosen from H; or $C_1$-$C_{20}$ hydrocarbyl; and each of $R_{24}$-$R_{25}$ is independently chosen from: H; $C_1$-$C_{12}$ hydrocarbyl; or OR'''', wherein R'''' is chosen from H or $C_1$-$C_{12}$ hydrocarbyl; and $R_{26}$ is H, or a bond which together with $R_{25}$ forms =O.

In certain embodiments, $R_{21}$ is present as hydroxyl and methyl. In other embodiments, $R_{21}$ is present as acyl and methyl.

In certain embodiments, $R_{23}$ is a $C_1$-$C_{18}$ hydrocarbyl.

In some embodiments, the chroman-based compound according to Formula V is a tocotrienol, including, but not limited to, α-tocotrienol; β-tocotrienol; γ-tocotrienol, and δ-tocotrienol. In other embodiments, the chroman-based compound is a tocopherol including, but not limited to, α-tocopherol, β-tocopherol, γ-tocopherol, and δ-tocopherol.

In some embodiments, the chroman-based compound is vitamin E or its acetate according to Formula Va

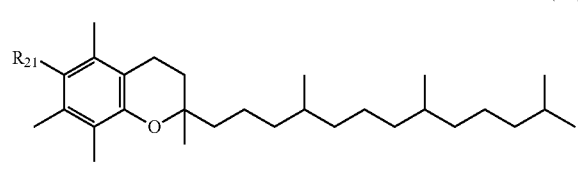

wherein $R_{21}$ is chosen from OH; or —OC(O)CH$_3$, respectively.

In certain embodiments, the stabilizer composition includes two or more chroman-based compounds according to Formula V.

The chroman-based compound is present from 0.001% to 5.0% by weight of the total weight of the stabilizer composition, preferably from 0.01% to 2.0% by weight of the total weight of the stabilizer composition, and more preferably from 0.01% to 1.0% by weight of the total weight of the stabilizer composition. In certain embodiments, the chroman-based compound is present at 0.05% by weight of the total weight of the stabilizer composition.

In certain embodiments, the stabilizer composition can further include at least one compound chosen from the group of organic phosphites or phosphonites. In some embodiments the organic phosphite or phosphonite compound includes at least one organic phosphite or phosphonite chosen from i) a compound according to Formulas 1-7:

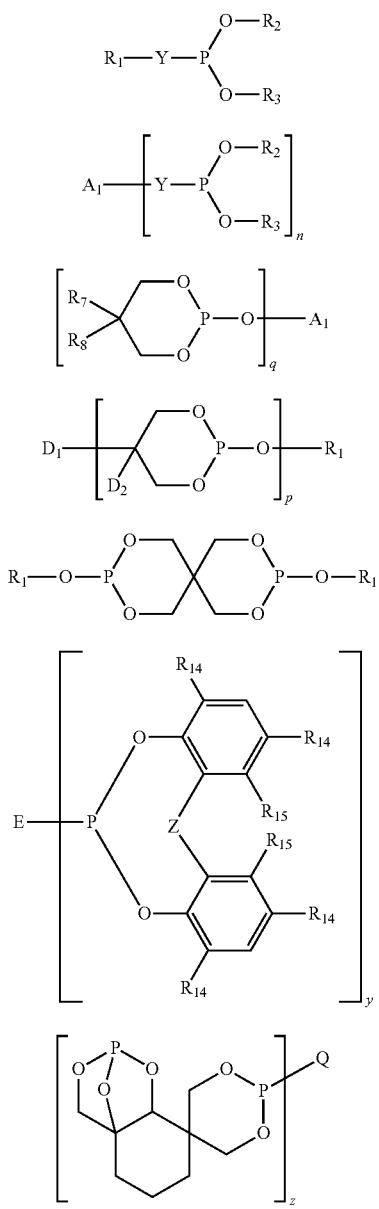

in which the indices are integral and
n is 2, 3 or 4; p is 1 or 2; q is 2 or 3; r is 4 to 12; y is 1, 2 or 3; and z is 1 to 6;

$A_1$, if n is 2, is $C_2$-$C_{18}$ alkylene; $C_2$-$C_{12}$ alkylene interrupted by oxygen, sulfur or —$NR_4$—; a radical of the formula

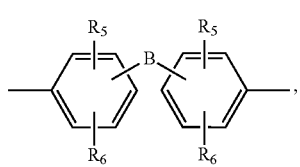

or phenylene;

$A_1$, if n is 3, is a radical of the formula —$C_rH_{2r-1}$—;

$A_1$, if n is 4, is $$—CH_2—\underset{\underset{CH_2—}{|}}{\overset{\overset{CH_2—}{|}}{C}}—CH_2—;$$

B is a direct bond, —$CH_2$—, —$CHR_4$—, —$CR_1R_4$—, sulfur, $C_5$-$C_7$ cycloalkylidene, or cyclohexylidene which is substituted by from 1 to 4 $C_1$-$C_4$ alkyl radicals in position 3, 4 and/or 5;

$D_1$, if p is 1, is $C_1$-$C_4$ alkyl and, if p is 2, is —$CH_2OCH_2$—;
$D_2$ is $C_1$-$C_4$ alkyl;
E, if y is 1, is $C_1$-$C_{18}$ alkyl, —$OR_1$ or halogen;
E, if y is 2, is —$O$-$A_2$-$O$—, wherein $A_2$ is as defined for $A_1$ when n is 2;
E, if y is 3, is a radical of the formula $R_4C(CH_2O—)_3$ or $N(CH_2CH_2O—)_3$;
Q is the radical of an at least z-valent mono or poly alcohol or phenol, this radical being attached via the oxygen atom of the OH group of the mono or poly alcohol or phenol to the phosphorus atom;
$R_1$, $R_2$ and $R_3$ independently of one another are $C_1$-$C_{18}$ alkyl which is unsubstituted or substituted by halogen, —$COOR_4$, —CN or —$CONR_4R_4$; $C_2$-$C_{18}$ alkyl interrupted by oxygen, sulfur or —$NR_4$—; $C_7$-$C_9$ phenylalkyl; $C_5$-$C_{12}$ cycloalkyl, phenyl or naphthyl; naphthyl or phenyl substituted by halogen, 1 to 3 alkyl radicals or alkoxy radicals having a total of 1 to 18 carbon atoms or by $C_7$-$C_9$ phenylalkyl; or a radical of the formula

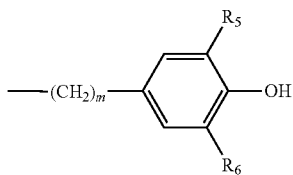

in which m is an integer from the range 3 to 6;
$R_4$ is hydrogen, $C_1$-$C_8$ alkyl, $C_5$-$C_{12}$ cycloalkyl or $C_7$-$C_9$ phenylalkyl,
$R_5$ and $R_6$ independently of one another are hydrogen, $C_1$-$C_8$ alkyl or $C_5$-$C_6$ cycloalkyl,
$R_7$ and $R_8$, if q is 2, independently of one another are $C_1$-$C_4$ alkyl or together are a 2,3-dehydropentamethylene radical; and
$R_7$ and $R_8$, if q is 3, are methyl;
each instance of $R_{14}$ is independently chosen from hydrogen, $C_1$-$C_9$ alkyl or cyclohexyl,
each instance of $R_{15}$ is independently chosen from hydrogen or methyl,
X and Y are each a direct bond or oxygen,
Z is a direct bond, methylene, —$C(R_{16})_2$— or sulfur, and $R_{16}$ is $C_1$-$C_8$ alkyl; or ii) a trisarylphosphite according to Formula 8:

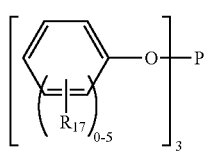
(8)

wherein $R_{17}$ is present at from 0 to 5 positions of the aromatic portion of Formula 8 and in each instance is independently chosen from $C_1$-$C_{20}$ alkyl, $C_3$-$C_{20}$ cycloalkyl, $C_4$-$C_{20}$ alkyl cycloalkyl, $C_6$-$C_{10}$ aryl, or $C_7$-$C_{20}$ alkylaryl; or iii) combinations of i) and ii).

In some embodiments, the following organic phosphites or phosphonites are preferred: triphenyl phosphite; diphenyl alkyl phosphites; phenyl dialkyl phosphites; trilauryl phosphite; trioctadecyl phosphite; distearyl pentaerythritol phosphite; tris(2,4-di-tert-butylphenyl) phosphite; tris(nonylphenyl) phosphite; a compound of formulae (A), (B), (C), (D), (E), (F), (G), (H), (J), (K) or (L):

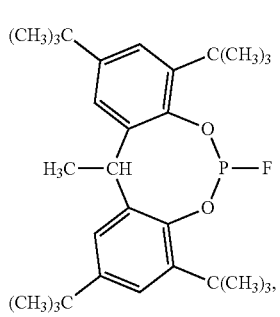
(A)

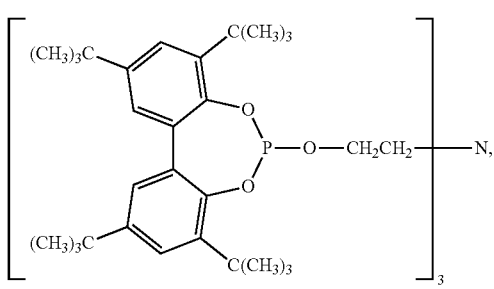
(B)

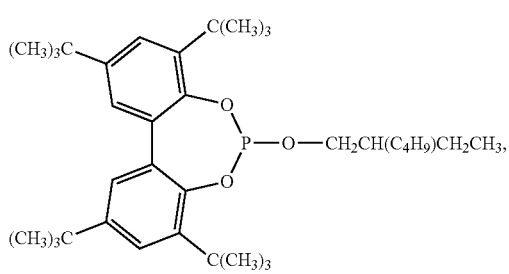
(C)

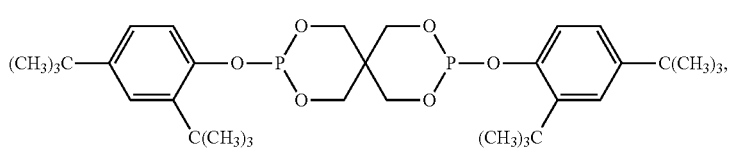
(D)

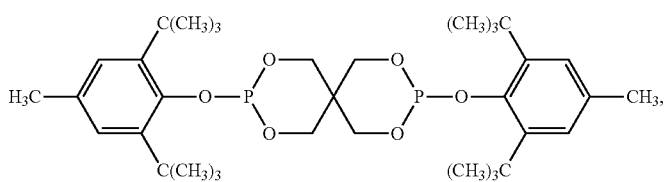
(E)

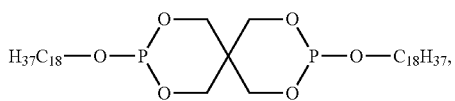
(F)

-continued

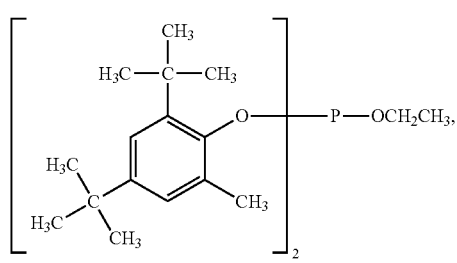

(G)

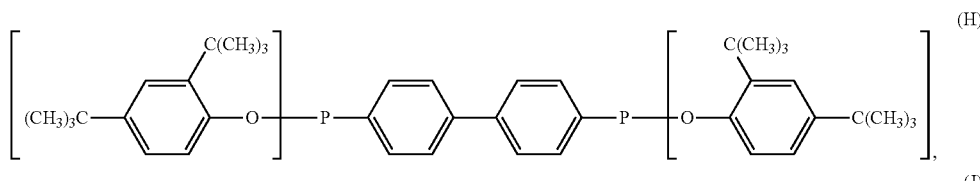

(H)

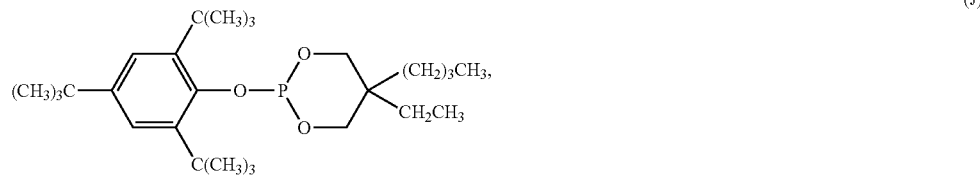

(J)

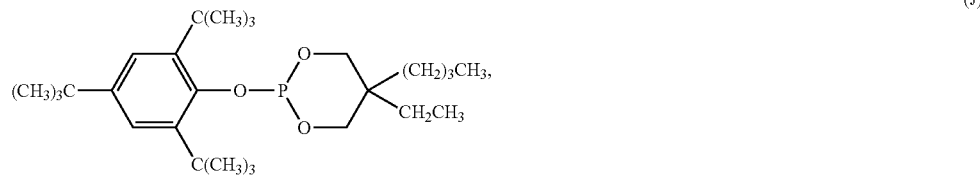

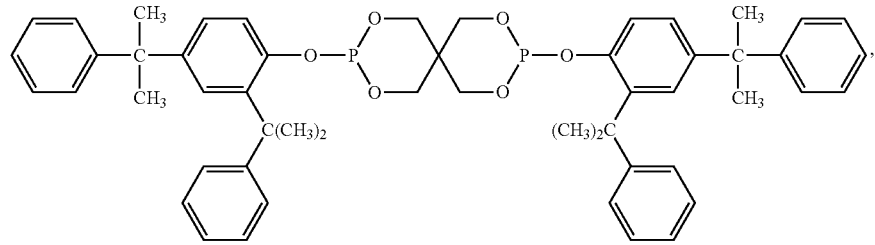

(K)

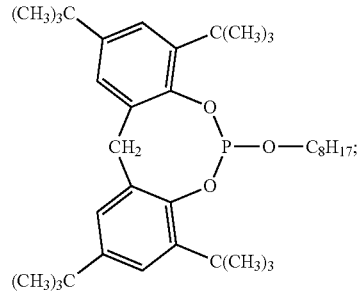

(L)

2-butyl-2-ethyl-1,3-propanediol 2,4,6-tri-t-butylphenol phosphite; bis-(2,6-di-t-butyl-4-methylphenyl) pentaerythritol diphosphite; 2-butyl-2-ethyl-1,3-propanediol 2,4-dicumylphenol phosphite; 2-butyl-2-ethyl-1,3-propanediol 4-methyl-2,6-di-t-butylphenol phosphite; or bis-(2,4,6-tri-t-butyl-phenyl) pentaerythritol diphosphite.

The following organic phosphites and phosphonites are particularly suitable for use in the rotomolding processes described herein: tris(2,4-di-tert-butylphenyl)phosphite (IRGAFOS® 168); Bis(2,4-dicumylphenyl)pentaerythritol diphosphite (DOVERPHOS® S9228); and tetrakis(2,4-di-tert-butylphenyl)4,4'-biphenylene-diphosphonite (IRGAFOS® P-EPQ).

The organic phosphites or phosphonites can be present in an amount from 0.01% to 10% by weight based on the total weight of the polymer material to be stabilized. Preferably, the amount of organic phosphite or phosphonite is available from 0.05 to 5%, and more preferably from 0.1 to 3% by weight based on the total weight of the polymer material to be stabilized.

In certain embodiments, the stabilizer composition can further include at least one hindered phenol compound. Suitable hindered phenols for use with the rotomolding processes described herein include, but are not limited to, those having a molecular fragment according to one or more of Formula (IVa), (IVb), or (IVc):

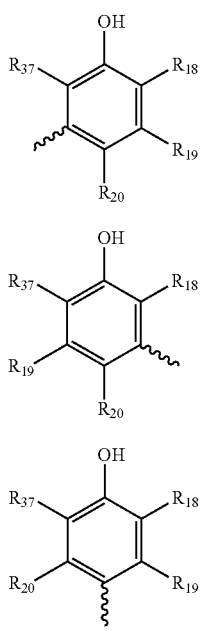

wherein

" $\sim\!\!\sim\!\!\sim$ "

indicates the point of attachment (via a carbon bond) of the molecular fragment to a parent compound, and wherein $R_{18}$ of Formula (IVa), (IVb), and (IVc) is chosen from hydrogen or a $C_{1-4}$ hydrocarbyl; $R_{19}$ and $R_{20}$ of Formula (IVa), (IVb), and (IVc) are the same or different and are independently chosen from hydrogen or a $C_1$-$C_{20}$ hydrocarbyl; and $R_{37}$ of Formula (IVa), (IVb), and (IVc) is chosen from a $C_1$-$C_{12}$ hydrocarbyl. In some embodiments, $R_{18}$ and $R_{37}$ are independently chosen from methyl or t-butyl.

The following compounds exemplify some hindered phenols that are suitable for use in the compositions and processes of the invention: (1,3,5-Tris(4-t-butyl-3-hydroxy-2,6-dimethylbenzyl)-1,3,5-triazine-2,4,6-(1H,3H,5H)-trione; 1,3,5-tris(3,5-di-tert-butyl-4-hydroxybenzyl)-1,3,5-triazine-2,4,6(1H,3H,5H)-trione (IRGANOX® 3114); 1,1,3-Tris(2'-methyl-4'-hydroxy-5'-t-butylphenyl)butane; Triethylene glycol bis[3-(3-t-butyl-4-hydroxy-5-methylphenyl)propionate]; 4,4'-Thiobis(2-t-butyl-5-methylphenol); 2,2'-Thiodiethylene bis[3-(3-t-butyl-4-hydroxyl-5-methylphenyl)propionate]; Octadecyl 3-(3'-t-butyl-4'-hydroxy-5'-methylphenyl)propionate; Tetrakismethylene(3-t-butyl-4-hydroxy-5-methylhydrocinnamate)methane; N,N'-Hexamethylene bis[3-(3-t-butyl-4-hydroxy-5-methylphenyl)propionamide]; Di(4-tertiarybutyl-3-hydroxy-2,6-dimethyl benzyl) thiodipropionate; and octadecyl 3,5-di-(tert)-butyl-4-hydroxyhydrocinnamate.

Other phenols also suitable for use with processes and compositions of the invention are known to those of skill in the art and include, for example:

2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4 isobutylphenol; 2,6-dicyclopentyl-4-methylphenol; 2-(α-methylcyclohexyl)-4,6 dimethylphenol; 2,6-di-octadecyl-4-methylphenol; 2,4,6,-tricyclohexyphenol; and 2,6-di-tert-butyl-4-methoxymethylphenol;

2,2'-methylene-bis-(6-tert-butyl-4-methylphenol) (CYANOX® 2246); 2,2'-methylene-bis-(6-tert-butyl-4-ethylphenol) (CYANOX® 425); 2,2'-methylene-bis-(4-methyl-6-(α-methylcyclohexyl)phenol); 2,2'-methylene-bis-(4-methyl-6-cyclohexylphenol); 2,2'-methylene-bis-(6-nonyl-4-methylphenol); 2,2'-methylene-bis-(6-nonyl-4methylphenol); 2,2'-methylene-bis-(6-(α-methylbenzyl)-4-nonylphenol); 2,2'-methylene-bis-(6-(α,α-dimethylbenzyl)-4-nonyl-phenol); 2,2'-methylene-bis-(4,6-di-tert-butylphenol); 2,2'-ethylidene-bis-(6-tert-butyl-4-isobutylphenol); 4,4'methylene-bis-(2,6-di-tert-butylphenol); 4,4'-methylene-bis-(6-tert-butyl-2-methylphenol); 1,1-bis-(5-tert-butyl-4-hydroxy-2-methylphenol)butane 2,6-di-(3-tert-butyl-5-methyl-2-hydroxybenzyl)-4-methylphenol; 1,1,3-tris-(5-tert-butyl-4-hydroxy-2-methylphenyl)butane; 1,1-bis-(5-tert-butyl-4-hydroxy2-methylphenyl)-3-dodecyl-mercaptobutane; ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene; di-(2-(3'-tert-butyl-2'hydroxy-5'methylbenzyl)-6-tert-butyl-4-methylphenyl-1)terephthalate; and other phenolics such as monoacrylate esters of bisphenols such as ethylidene bis-2,4-di-t-butylphenol monoacrylate ester;

Hydroquinones such as 2,6-di-tert-butyl-4-methoxyphenol; 2,5-di-tert-butylhydroquinone; 2,5-di-tert-amyl-hydroquinone; and 2,6-diphenyl-4-octadecyloxyphenol; and Thiodiphenyl ethers such as 2,2'-thio-bis-(6-tert-butyl-4-methylphenol); 2,2'-thio-bis-(4-octylphenol); 4,4'thio-bis-(6-tert-butyl-3-methylphenol); and 4,4'-thio-bis-(6-tert-butyl-2-methylphenol).

A stabilizer composition including at least one chroman-based compound according to Formula V is suitable for stabilizing polyolefin hollow articles which are prepared by the rotomolding process. Examples of polyolefins suitable for such use with the stabilizer composition according to the invention include at least the following:

(A) Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be cross-linked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE);

(B) Polyolefins, i.e. the polymers of monoolefins exemplified in (A), preferably polyethylene and polypropylene, can be prepared by different, and especially by the following, methods:

i) radical polymerisation (normally under high pressure and at elevated temperature); or ii) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

(C) Mixtures of the polymers mentioned under (A), for example mixtures of polypropylene with polyisobutylene, polypropylene with polyethylene (for example PP/HDPE, PP/LDPE) and mixtures of different types of polyethylene (for example LDPE/HDPE).

(D) Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in (A) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

The stabilized polymer compositions according to the invention may further include one or more co-stabilizers and/or additives that include, but are not limited to: hindered amine light stabilizers, hindered hydroxyl benzoates, nickel phenolates, ultraviolet light stabilizers, and combinations thereof in an amount effective to stabilize the polymer composition against the degradative effects of visible and/or ultraviolet light radiation.

Suitable hindered amine light stabilizers for use with the processes and stabilized polymer compositions according to the invention include, for example, compounds having a molecular fragment according to Formula (VI):

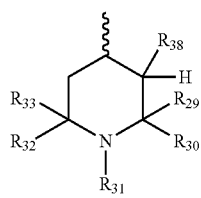

(VI)

wherein $R_{31}$ is chosen from: hydrogen; OH; $C_1$-$C_{20}$ hydrocarbyl; —$CH_2CN$; $C_1$-$C_{12}$ acyl; or $C_1$-$C_{18}$ alkoxy; $R_{38}$ is chosen from: hydrogen; or $C_1$-$C_8$ hydrocarbyl; and each of $R_{29}$, $R_{30}$, $R_{32}$, and $R_{33}$ is independently chosen from $C_1$-$C_{20}$ hydrocarbyl, or $R_{29}$ and $R_{30}$ and/or $R_{32}$ and $R_{33}$ taken together with the carbon to which they are attached form a $C_5$-$C_{10}$ cycloalkyl;

or Formula (VIa)

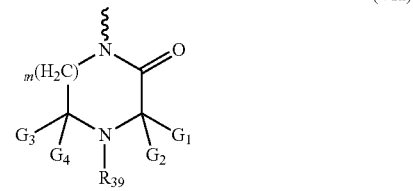

(VIa)

wherein m is an integer from 1 to 2;

$R_{39}$ is chosen from: hydrogen; OH; $C_1$-$C_{20}$ hydrocarbyl; —$CH_2CN$; $C_1$-$C_{12}$ acyl; or $C_1$-$C_{18}$ alkoxy; and each of $G_1$-$G_4$ is independently chosen from $C_1$-$C_{20}$ hydrocarbyl.

Hindered amine light stabilizers particularly suitable for use with the present invention include, but are not limited to, bis(2,2,6,6-tetramethylpiperidin-4-yl) sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; a condensate of 1-(2-hydroxyethyl)-2,2,6,6-tetramethyl-4-hydroxypiperidine and succinic acid; 2,2,6,6-tetramethylpiperidin-4-yl stearate; 2,2,6,6-tetramethylpiperidin-4-yl dodecanate; 1,2,2,6,6-pentamethylpiperidin-4-yl stearate; 1,2,2,6,6-pentamethylpiperidin-4-yl dodecanate; a condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; a condensate of N,N'-bis(2,2,6,6-tetramethylpiperidin-4-yl)hexamethylenediamine and 4-morpholino-2,6-dichloro-1,3,5-triazine; a condensate of 2-chloro-4,6-bis(4-n-butylamino-2,2,6,6-tetramethylpiperidyl)-1,3,5-triazine and 1,2-bis(3-aminopropylamino)ethane; a condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; a condensate of N,N'-bis(2,2,6,6-tetramethylpiperidin-4-yl)hexamethylenediamine and 4-cyclohexylamino-2,6-dichloro-1,3,5-triazine; a condensate of 1,2-bis(3-aminopropylamino)ethane, 2,4,6-trichloro-1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines; a reaction product of 7,7,9,9- tetramethyl-2-cycloundecyl-1-oxa-3,8-diaza-4-oxospiro[4.5]decane and epichlorohydrin;

N-alkoxy hindered amine light stabilizers including, but not limited to, tetrakis(2,2,6,6-tetramethyl-4-piperidyl) butane-1,2,3,4-tetracarboxylate (MARK® LA-57); 1,2,3,4-butanetetracarboxylic acid, tetrakis(1,2,2,6,6-pentamethyl-4-piperidinyl)ester (MARK® LA-52); 1,2,3,4-butanetetracarboxylic acid, 1,2,2,6,6-pentamethyl-4-piperdinyl tridecyl ester (MARK® LA-62); 1,2,3,4-butanetetracarboxylic acid, 2,2,6,6-tetramethyl-4-piperidinyl tridecyl ester (MARK® LA-67); 1,2,3,4-butanetetracarboxylic acid, polymer with 2,2,6,6-tetramethyl-2,4,8,10-tetraoxaspiro[5.5]-undecane-3,9-diethanol,1,2,2,6,6-pentamethyl-4-piperdinyl ester (MARK® LA-63); 1,2,3,4-butanetetracarboxylic acid, polymer with 2,2,6,6-tetramethyl-2,4,8,10-tetraoxaspiro[5.5]-undecane-3,9-diethanol, 2,2,6,6-tetramethyl-4-piperdinyl ester (MARK® LA-68); bis(1-undecanoxy-2,2,6,6-tetramethylpiperidin-4-yl)carbonate (MARK® LA-81; aka STAB® LA-81 available from Adeka Palmarole, Saint-Louis, France); TINUVIN® 123; TINUVIN® NOR 371; TINUVIN® XT-850/XT-855; FLAMESTAB® NOR 116; and those disclosed in EP 0 889 085;

hydroxyl-substituted N-alkoxy HALS including, but not limited to, those disclosed in U.S. Pat. No. 6,271,377 such as 1-(2-hydroxy-2-methylpropoxy)-2,2,6,6-tetramethyl-4-piperidinol; 1-(2-hydroxy-2-methylpropoxy)-4-octadecanoyloxy-2,2,6,6-tetramethylpiperidine; 1-(4-octadecanoyloxy-2,2,6,6-tetramethylpiperidin-1-yloxy)-2-octadecanoyloxy-2-methylpropane; 1-(2-hydroxyethyl)-2,2,6,6-tetramethyl-4-piperidinol; a reaction product of 1-(2-hydroxyethyl)-2,2,6,6-tetramethyl-4-piperidinol and dimethylsuccinate;

any of the tetramethylpiperidyl groups disclosed in WO 2007/104689 including, but not limited to, 2,2,4,4-tetramethyl-7-oxa-3,20-diazadispiro[5.1.11.2]heneicosan-21-one (HOSTAVIN® N20); the ester of 2,2,6,6-tetramethyl-4-piperidinol with higher fatty acids (CYASORB® 3853); 3-dodecyl-1-(2,2,6,6-tetramethyl-4-piperidyl)pyrrolidine-2,5-dione (SANDUVOR® 3055); and their wax reaction products such as HALS NOW (LS X—N—O—W1);

piperizinone compounds and derivatives thereof disclosed in U.S. Pat. Nos. 6,843,939; 7,109,259; 4,240,961; 4,480,092; 4,629,752; 4,639,479; 5,013,836; 5,310,771; and WO 88/08863 including, but not limited to, 1H-Pyrrole-2,5-dione, 1-octadecyl-, polymer with (1-methylethenyl)benzene and 1-(2,2,6,6-tetramethyl-4-piperidinyl)-1H-pyrrole-2,5-dione; piperazinone, 1,1',1"-[1,3,5-triazine-2,4,6-triyltris[(cyclohexylimino)-2,1-ethanediyl]]tris[3,3,5,5-tetramethyl-; piperazinone, 1,1',1"-[1,3,5-triazine-2,4,6-triyltris[(cyclohexylimino)-2,1-ethanediyl]]tris[3,3,4,5,5-pentamethyl-; the reaction product of 7,7,9,9-tetramethyl-2-cycloundecyl-1-oxa-3,8-diaza-4-oxospiro[4.5]decane and epichlorohydrin; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; the condensate of N,N'-bis(2,2,6,6-tetramethylpiperidin-4-yl) hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 2-[(2-hydroxyethyl)amino]-4,6-bis[N-(1-cyclohexyloxy-2,2,6,6-tetramethylpiperidin-4-yl)butylamino-1,3,5-triazine; propanedioic acid, [(4-methoxyphenyl)-methylene]-bis-(1,2,2,6,6-pentamethyl-4-piperidinyl) ester; tetrakis(2,2,6,6-tetramethylpiperidin-4-yl)-1,2,3,4-butanetetracarboxylate; benzenepropanoic acid, 3,5-bis(1,1-dimethylethyl)-4-hydroxy-, 1-[2-[3-[3,5-bis(1,1-dimethylethyl)-4-hydroxyphenyl]-1-oxopropoxy]ethyl]-2,2,6,6-tetramethyl-4-piperidinyl ester; N-(1-octyloxy-2,2,6,6-tetramethylpiperidin-4-yl)-N'-dodecyloxalamide; tris(2,2,6,6-tetramethylpiperidin-4-yl) nitrilotriacetate; 1,5-dioxaspiro{5,5}undecane-3,3-dicarboxylic acid, bis(1,2,2,6,6-pentamethyl-4-piperidinyl): 1,5-dioxaspiro{5,5}undecane-3,3-dicarboxylic acid, bis(2,2,6,6-tetramethyl-4-piperidinyl); the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl) hexamethylenediamine and 4-tert-octylamino-2,6-dichloro-1,3,5-triazine; 1,2,3,4-butanetetracarboxylic acid, 1,2,2,6,6-pentamethyl-4-piperidinyl tridecyl ester; tetrakis(2,2,6,6-tetramethylpiperidin-4-yl)-1,2,3,4-butanetetracarboxylate; 1,2,3,4-butanetetracarboxylic acid, 2,2,6,6-tetramethyl-4-piperidinyl tridecyl ester; tetrakis(1,2,2,6,6-pentamethylpiperidin-4-yl)-1,2,3,4-butanetetracarboxylate; mixture of 2,2,4,4-tetramethyl-21-oxo-7-oxa-3,20-diazaspiro(5.1.11.2)-heneicosane-20-propanoic acid-dodecylester and 2,2,4,4-tetramethyl-21-oxo-7-oxa-3,20-diazaspiro(5.1.11.2)-heneicosane-20-propanoic acid-tetradecylester; 1H,4H,5H,8H-2,3a,4a,6,7a,8a-hexaazacyclopenta[def]fluorene-4,8-dione, hexahydro-2,6-bis(2,2,6,6-tetramethyl-4-piperidinyl)-; polymethyl[propyl-3-oxy(2',2',6',6'-tetramethyl-4,4'-piperidinyl)]siloxane; polymethyl[propyl-3-oxy(1',2',2',6',6'-pentamethyl-4,4'-piperidinyl)]siloxane; copolymer of methylmethacrylate with ethyl acrylate and 2,2,6,6-tetramethylpiperidin-4-yl acrylate; copolymer of mixed $C_{20}$ to $C_{24}$ alpha-olefins and (2,2,6,6-tetramethylpiperidin-4-yl)succinimide; 1,2,3,4-butanetetracarboxylic acid, polymer with β,β,β',β'-tetramethyl-2,4,8,10-tetraoxaspiro[5.5]undecane-3,9-diethanol, 1,2,2,6,6-pentamethyl-4-piperidinyl ester; 1,2,3,4-butanetetracarboxylic acid, polymer with β,β,β',β'-tetramethyl-2,4,8,10-tetraoxaspiro[5.5]undecane-3,9-diethanol, 2,2,6,6-tetramethyl-4-piperidinyl ester copolymer; 1,3-benzenedicarboxamide, N,N'-bis(2,2,6,6-tetramethyl-4-piperidinyl; 1,1'-(1,10-dioxo-1,10-decanediyl)-bis(hexahydro-2,2,4,4,6-pentamethylpyrimidine; ethane diamide, N-(1-acetyl-2,2,6,6-tetramethylpiperidinyl)-N'-dodecyl; formamide, N,N'-1,6-hexanediylbis[N-(2,2,6,6-tetramethyl-4-piperidinyl]; D-glucitol, 1,3:2,4-bis-O-(2,2,6,6-tetramethyl-4-piperidinylidene)-; 2,2,4,4-tetramethyl-7-oxa-3,20-diaza-21-oxo-dispiro[5.1.11.2]heneicosane;
propanamide, 2-methyl-N-(2,2,6,6-tetramethyl-4-piperidinyl)-2-[(2,2,6,6-tetramethyl-4-piperidinyl)amino]-; 7-oxa-3,20-diazadispiro[5.1.11.2]heneicosane-20-propanoic acid, 2,2,4,4-tetramethyl-21-oxo-, dodecyl ester; N-(2,2,6,6-tetramethylpiperidin-4-yl)-β-aminopropionic acid dodecyl ester; N-(2,2,6,6-tetramethylpiperidin-4-yl)-N'-aminooxalamide; propanamide, N-(2,2,6,6-tetramethyl-4-piperidinyl)-3-[(2,2,6,6-tetramethyl-4-piperidinyl)amino]-; mixture of 4-hexadecyloxy- and 4-stearyloxy-2,2,6,6-tetramethylpiperidine; 3-dodecyl-1-(1,2,2,6,6-pentamethylpiperidin-4-yl) pyrrolidine-2,5-dione; 3-dodecyl-1-(1-ethanoyl-2,2,6,6-pentamethylpiperidin-4-yl)pyrrolidine-2,5-dione; bis(2,2,6,6-tetramethylpiperidin-4-yl)succinate; bis(1,2,2,6,6-pentamethylpiperidin-4-yl) n-butyl 3,5-di-tert-butyl-4-hydroxybenzylmalonate; tris(2,2,6,6-tetramethylpiperidin-4-yl) nitrilotriacetate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate;

3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; 2-undecyl-7,7,9,9-tetramethyl-1-oxa-3,8-diaza-4-oxospiro[4.5]decane; 1,5-dioxaspiro{5,5}undecane-3,3-dicarboxylic acid, bis(2,2,6,6-tetramethyl-4-piperidinyl) and 1,5-dioxaspiro{5,5}undecane-3,3-dicarboxylic acid, bis(1,2,2,6,6-pentamethyl-4-piperidinyl); $N^1$-(β-hydroxyethyl)3,3-pentamethylene-5,5-dimethylpiperazin-2-one; $N^1$-tert-octyl-3,3,5,5-tetramethyl-diazepin-2-one; N1-tert-octyl-3,3-pentamethylene-5,5-hexamethylene-diazepin-2-one; $N^1$-tert-octyl-3,3-pentamethylene-5,5-dimethylpiperazin-2-one; trans-1,2-cyclohexane-bis-($N^1$-5,5-dimethyl-3,3-pentamethylene-2-piperazinone; trans-1,2-cyclohexane-bis-($N^1$-3,3,5,5-dispiropentamethylene-2-piperazinone); $N^1$-isopropyl-1,4-diazadispiro-(3,3,5,5)pentamethylene-2-piperazinone; $N^1$-isopropyl-1,4-diazadispiro-3,3-pentamethylene-5,5-tetramethylene-2-piperazinone; $N^1$-isopropyl-5,5-dimethyl-3,3-pentamethylene-2-piperazinone; trans-1,2-cyclohexane-bis-$N^1$-(dimethyl-3,3-pentamethylene-2-piperazinone); $N^1$-octyl-5,5-dimethyl-3,3-pentamethylene-1,4-diazepin-2-one; and $N^1$-octyl-1,4-diazadispiro-(3,3,5,5) pentamethylene-1,5-diazepin-2-one. Other sterically hindered amines suitable for use with the invention include, for example, any of those disclosed in EP 1 308 084.

The hindered amine component can be present in an amount from 0.01 to 10% by weight based on the total weight of the polymer material to be stabilized. Preferably, the amount of hindered amine is available from 0.05 to 5%, and more preferably from 0.1 to 3% by weight based on the total weight of the polymer material to be stabilized.

Other light stabilizers suitable for use with the present invention include one or more of the following:

2-(2'-Hydroxyphenyl)benzotriazoles, for example 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chloro-benzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)benzotriazole; 2-(2'-hydroxy-4'-octyloxyphenyl)benzotriazole; 2-(3',5'-di-tert-amyl-2'-hydroxyphenyl)benzotriazole; 2-(3',5'-bis-(α,α-dimethylbenzyl)-2'-hydroxyphenyl)benzotriazole; 2-(3'-tert-butyl-2'-hydroxy-5'-(2-octyloxycarbonylethyl)phenyl)-5-chloro-benzotriazole; 2-(3'-tert-butyl-5'-[2-(2-ethylhexyloxy)-carbonylethyl]-2'-hydroxyphenyl)-5-chloro-benzotriazole; 2-(3'-tert-butyl-2'-hydroxy-5'-(2-methoxycarbonylethyl)phenyl)-5-chloro-benzotriazole; 2-(3'-tert-butyl-2'-hydroxy-5'-(2-methoxycarbonylethyl)phenyl)benzotriazole; 2-(3'-tert-butyl-2'-hydroxy-5'-(2-octyloxycarbonylethyl)phenyl)benzotriazole; 2-(3'-tert-butyl-5'-[2-(2-ethylhexyloxy)carbonyl]-2'-hydroxyphenyl)benzotriazole; 2-(3'-dodecyl-2'-hydroxy-5'-methylphenyl)benzotriazole; 2-(3'-tert-butyl-2'-hydroxy-5'-(2-isooctyloxycarbonylethyl)phenylbenzotriazole; 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO—$CH_2CH_2$]₂ where R=3'-tert-butyl-4'-hydroxy-5'-2H-benzotriazol-2-ylphenyl; 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl] benzotriazole;

2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives;

Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate;

Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands; and 2-(2'-hydroxyphenyl)-1,3,5-triazine compounds according to Formula (VII):

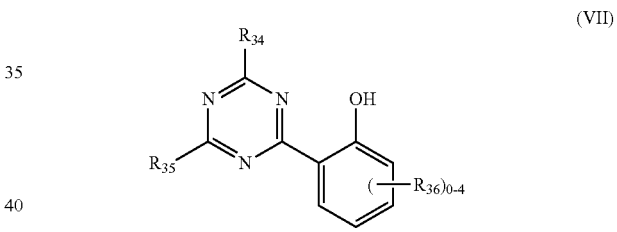

(VII)

wherein each of $R_{34}$ and $R_{35}$ is independently chosen from $C_6$-$C_{10}$ aryl optionally substituted, $C_1$-$C_{10}$ hydrocarbyl-substituted amino, $C_1$-$C_{10}$ acyl or $C_1$-$C_{10}$ alkoxyl; and wherein $R_{36}$ is present at from 0 to 4 positions of the phenoxy portion of Formula VII and in each instance is independently chosen from hydroxyl, $C_1$-$C_{12}$ hydrocarbyl, $C_1$-$C_{12}$ alkoxyl, $C_1$-$C_{12}$ alkoxyester, or $C_1$-$C_{12}$ acyl. Such 2-(2-Hydroxyphenyl)-1,3,5-triazines include, but are not limited to, 4,6-bis-(2,4-dimethylphenyl)-2-(2-hydroxy-4-octyloxyphenyl)-s-triazine (CYASORB® 1164 available from Cytec Industries Inc.); 4,6-bis-(2,4-dimethylphenyl)-2-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxy-ethoxy)phenyl]-6-(4-chlorophenyl)-s-triazine; 2,4-bis[2-hydroxy-4-(2-hydroxy-4-(2-hydroxy-ethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine; 2,4-bis(2,4-dihydroxyphenyl)-6-(2,4-dimethylphenyl)-s-triazine; 2,4-bis(4-biphenylyl)-6-[2-hydroxy-4-[(octyloxycarbonyl)ethylideneoxy]phenyl]-s-triazine; 2,4-bis(4-biphenylyl)-6-[2-hydroxy-4-(2-ethylhexyloxy)phenyl]-s-triazine; 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)phenyl]-s- triazine; 2,4-bis(2,4-dimethylphenyl)-6-[2-hydroxy-4(-3-benzyloxy-2-hydroxypropyloxy)phenyl]-s-triazine; 2,4-bis(2-hydroxy-4-n-butyloxyphenyl)-6-(2,4-di-n-butyloxyphenyl)-s-triazine; 2,4-bis(2,4-dimethylphenyl)-6-[2-hydroxy-4-(3-nonyloxy-2-hydroxypropyloxy)-5-α-cumylphenyl]-s-triazine; methylenebis-{2,4-bis(2,4-dimethylphenyl)-6-[2-hydroxy-4-(3-butyloxy-2-hydroxypropoxy)phenyl]-s-triazine}; methylene bridged dimer mixture bridged in the 3:5', 5:5' and 3:3' positions in a 5:4:1 ratio; 2,4,6-tris(2-hydroxy-4-isooctyloxycarbonyliso-propylideneoxy-phenyl)-s-triazine; 2,4-bis(2,4-dimethylphenyl)-6-(2-hydroxy-4-hexyloxy-5-α-cumylphenyl)-s-triazine; 2-(2,4,6-trimethylphenyl)-4,6-bis[2-hydroxy-4-(3-butyloxy-2-hydroxypropyloxy)phenyl]-s-triazine; 2,4,6-tris[2-hydroxy-4-(3-sec-butyloxy-2-hydroxypropyloxy)-phenyl]-s-triazine; mixture of 4,6-bis-(2,4-dimethylphenyl)-2-(2-hydroxy-4-(3-dodecyloxy-2-hydroxypropoxy)phenyl)-s-triazine and 4,6-bis-(2,4-dimethylphenyl)-2-(2-hydroxy-4-(3-tridecyloxy-2-hydroxypropoxy)phenyl)-s-triazine (TINUVIN® 400 available from BASF Corp.); 4,6-bis-(2,4-dimethylphenyl)-2-(2-hydroxy-4(3-(2-ethylhexyloxy)-2-hydroxypropoxy)-phenyl)-s-triazine; 4,6-diphenyl-2-(4-hexyloxy-2-hydroxyphenyl)-s-triazine; 2-(4,6-Diphenyl-1,3,5-triazin-2-yl)-5-[2-(2-ethylhexanoyloxy)ethoxy]phenol (ADK STAB® LA-46 available from Adeka Palmarole, Saint-Louis, France); 2,4,6-tris(2-hydroxy-4-octyloxyphenyl)-1,3,5-triazine; propanoic acid, 2,2',2''-[1,3,5-triazine-2,4,6-triyltris[(3-hydroxy-4, 1-phenylene)oxy]]tris-1,1',1''-trioctyl ester (TINUVIN® 477 available from BASF Corp.); propanoic acid, 2-[4-[4,6-bis([1,1'-biphenyl]-4-yl)-1,3,5-triazin-2yl]-3-hydroxyphenoxyl]-isooctyl ester (TINUVIN® 479 available from BASF Corp.); and combinations thereof.

In certain embodiments, the stabilized polymer compositions according to the invention include a blend of at least one hindered amine light stabilizer and at least one ultraviolet light absorber.

Further embodiments of the stabilized polymer compositions according to the invention include at least one compound chosen from:

a hydroxylamine compound according to Formula VIII:

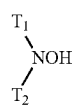

(VIII)

wherein $T_1$ is chosen from $C_1$-$C_{36}$ hydrocarbyl, $C_5$-$C_{12}$ cycloalkyl, or $C_7$-$C_9$ aralkyl, optionally substituted; and $T_2$ is chosen from hydrogen or $T_1$; or a tertiary amine oxide compound according to Formula IX:

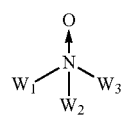

(IX)

wherein $W_1$ and $W_2$ are each independently chosen from a $C_6$-$C_{36}$ hydrocarbyl chosen from a straight or branched chain $C_6$-$C_{36}$ alkyl, $C_6$-$C_{12}$ aryl, $C_7$-$C_{36}$ aralkyl, $C_7$-$C_{36}$ alkaryl, $C_5$-$C_{36}$ cycloalkyl, $C_6$-$C_{36}$ alkcycloalkyl; or $C_6$-$C_{36}$ cycloalkylalkyl;

$W_3$ is chosen from a $C_1$-$C_{36}$ hydrocarbyl chosen from a straight or branched chain $C_1$-$C_{36}$ alkyl, $C_6$-$C_{12}$ aryl, $C_7$-$C_{36}$ aralkyl, $C_7$-$C_{36}$ alkaryl, $C_5$-$C_{36}$ cycloalkyl, $C_6$-$C_{36}$ alkylcycloalkyl; or $C_6$-$C_{36}$ cycloalkylalkyl; with the proviso that at least one of W1, $W_2$ and $W_3$ contains a R carbon-hydrogen bond; and wherein said alkyl, aralkyl, alkaryl, cycloalkyl, alkylcycloalkyl and cycloalkylalkyl groups of $W_1$, $W_2$ and $W_3$ may be interrupted by from one to sixteen moieties selected from the group consisting of —O—, —S—, —SO—, —SO$_2$—, —COO—, —OCO—, —CO—, —NW$_4$—, —CONW$_4$— and —NW$_4$CO—, or wherein said alkyl, aralkyl, alkaryl, cycloalkyl, alkylcycloalkyl and cycloalkylalkyl groups of W1, $W_2$ and $W_3$ may be substituted with from one to sixteen substituents selected from the group consisting of —OW$_4$, —SW$_4$, —COOW$_4$, —OCOW$_4$, —COW$_4$, —N(W$_4$)$_2$, —CON(W$_4$)$_2$, —NW$_4$COW$_4$ and 5- and 6-membered rings containing the —C(CH$_3$)(CH$_2$R$_x$)NL(CH$_2$R$_x$)(CH$_3$)C— group, wherein $W_4$ is chosen from hydrogen or $C_1$-$C_8$ alkyl;

$R_x$ is chosen from hydrogen or methyl; and

L is chosen from a $C_1$-$C_{30}$ alkyl, a —C(O)R moiety wherein R is a $C_1$-$C_{30}$ straight or branched chain alkyl group, or a —OR moiety wherein R is a $C_1$-$C_{30}$ straight or branched chain alkyl group; or wherein said alkyl, aralkyl, alkaryl, cycloalkyl, alkcycloalkyl and cycloalkylalkyl groups of $W_1$, $W_2$ and $W_3$ are both interrupted and substituted by any of the moieties and/or substituents mentioned above; and wherein said aryl groups of $W_1$, $W_2$ and $W_3$ may be substituted with from one to three compounds independently chosen from halogen, $C_1$-$C_8$ alkyl, or $C_1$-$C_8$ alkoxy;

or combinations of compounds according to Formulas VIII and IX.

In particular embodiments, preference is given to N,N-dihydrocarbylhydroxylamine compounds according to Formula VIII wherein $T_1$ and $T_2$ are independently chosen from benzyl, ethyl, octyl, lauryl, dodecyl, tetradecyl, hexadecyl, heptadecyl or octadecyl; or wherein $T_1$ and T are each the alkyl mixture found in hydrogenated tallow amine.

In certain embodiments, hydroxylamine compounds according to Formula VIII are chosen from: N,N-dibenzylhydroxylamine; N,N-diethylhydroxylamine; N,N-dioctylhydroxylamine; N,N-dilaurylhydroxylamine; N,N-didodecylhydroxylamine; N,N-ditetradecylhydroxylaamine; N,N-dihexadecylhydroxylamine; N,N-dioctadecylhydroxylamine; N-hexadecyl-N-tetradecylhydroxylamine; N-hexadecyl-N-heptadecylhydroxylamine; N-hexadecyl-N-octadecylhydroxylamine; N-heptadecyl-N-octadecylhydroxylamine; N,N-di(hydrogenated tallow)hydroxylamine; or N,N-di(alkyl)hydroxylamine produced by the direct oxidation of N,N-di(hydrogenated tallow) amine.

In certain embodiments, preference is given to those structures of Formula IX where $W_1$ and $W_2$ are independently benzyl or substituted benzyl. It is also possible for each of $W_1$, $W_2$, and $W_3$ to be the same residue. In other embodiments, $W_1$ and $W_2$ can be alkyl groups of 8 to 26 carbon atoms, more preferably alkyl groups of 10 to 26 carbon atoms. $W_3$ can be an alkyl group of 1 to 22 carbon atoms, more preferably methyl or substituted methyl. Other preferred amine oxides include those wherein $W_1$, $W_2$, and $W_3$ are the same alkyl groups of 6 to 36 carbon atoms. Preferably, all of the aforementioned residues for $W_1$, $W_2$, and W₃ are saturated hydrocarbon residues or saturated hydrocarbon residues containing at least one of the aforementioned —O—, —S—, —SO—, —CO₂—, —CO—, or —CON— moieties. Those skilled in the art will be able to envision other useful residues for each of W₁, W₂, and W₃ without detracting from the present invention.

The saturated amine oxides may also include poly(amine oxides). By poly(amine oxide) is meant tertiary amine oxides containing at least two tertiary amine oxides per molecule. Illustrative poly(amine oxides), also called "poly(tertiary amine oxides)", include, but are not limited to, the tertiary amine oxide analogues of aliphatic and alicyclic diamines such as, for example, 1,4-diaminobutane; 1,6-diaminohexane; 1,10-diaminodecane; and 1,4-diaminocyclohexane, and aromatic based diamines such as, for example, diamino anthraquinones and diaminoanisoles.

Suitable amine oxides for use with the invention also include tertiary amine oxides derived from oligomers and polymers of the aforementioned diamines. Useful amine oxides also include amine oxides attached to polymers, for example, polyolefins, polyacrylates, polyesters, polyamides, polystyrenes, and the like. When the amine oxide is attached to a polymer, the average number of amine oxides per polymer can vary widely as not all polymer chains need to contain an amine oxide. All of the aforementioned amine oxides may optionally contain at least one —O—, —S—, —SO—, —CO₂—, —CO—, or —CONW₄— moiety. In a preferred embodiment, each tertiary amine oxide of the polymeric tertiary amine oxide contains a $C_1$ residue.

The groups $W_1$, $W_2$ and $W_3$ of Formula IX may be attached to a molecule containing a hindered amine. Hindered amines are known in the art and the amine oxide of the present invention may be attached to the hindered amine in any manner and structural position of the hindered amine. Useful hindered amines when part of an amine oxide compound include those of the general Formulas X and XI:

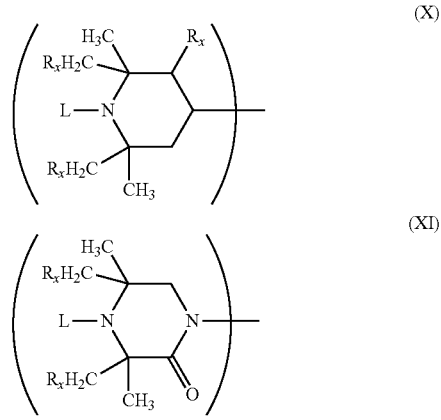

wherein L and $R_x$ are defined as described above.

Also included are amine oxides containing more than one hindered amine and more than one saturated amine oxide per molecule. The hindered amine may be attached to a poly(tertiary amine oxide) or attached to a polymeric substrate, as discussed above.

The hydroxyl amine derivatives and/or amine oxide derivatives can be used in amounts, in total, of about 0.0005% to about 5%, in particular from about 0.001% to about 2%, typically from about 0.01% to about 2% by weight, based on the weight of the polyolefin hollow article to be stabilized.

In other embodiments, the stabilized polymer compositions include further optional additives that can include at least one compound chosen from co-additives; nucleating agents; fillers; reinforcing agents; or combinations thereof.

Examples of such additives include, but are not limited to:

Basic co-additives, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zinc pyrocatecholate;

Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers);

Fillers and reinforcing agents, for example, calcium carbonate, silicates, glass fibres, glass bulbs, asbestos, talc, kaolin, mica, barium sulfate, metal oxides and hydroxides (e.g., aluminium hydroxide or magnesium hydroxide, carbon black, graphite, wood flour and flours or fibers of other natural products, synthetic fibers; impact modifiers Benzofuranones and indolinones, for example those disclosed in U.S. Pat. Nos. 4,325,863; 4,338,244; 5,175,312; 5,216,052; 5,252,643; 5,369,159; 5,488,117; 5,356,966; 5,367,008; 5,428,162; 5,428,177; 5,516,920; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one;

Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide;

Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-di(hydrogenated tallow)hydroxylamine;

Thiosynergists, for example, dilauryl thiodipropionate or distearyl thiodipropionate; and/or Peroxide scavengers, for example esters of 0-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(O-dodecylmercapto)propionate.

Other additives include, for example, plasticisers, lubricants, emulsifiers, pigments, rheology additives, catalysts, flow-control agents, optical brighteners, flameproofing agents, antistatic agents, clarifying agents and blowing agents.

In certain embodiments, the stabilizer composition is present from 0.001% to 65.0% by weight based on the total weight of the polymer composition to be stabilized and based on the number and type of stabilizing additives being added and/or the characteristics of the polymer composition to be stabilized. In some embodiments, the stabilizer composition is present from 0.01% to 50% by weight of the total weight of the polymer composition, and preferably from 0.05% to 25% by weight of the total, or from 0.1% to 10% by weight of the total. Those of ordinary skill in the art will be able to readily determine the amount and type of stabilizing additive(s) that should be added based on preparations as known and/or described in the literature, or through no more than routine experimentation.

The stabilized polymer compositions according to the invention can be readily made by any suitable method known to those of skill in the art. In certain embodiments, the components of the stabilized polymer compositions are mixed by at least one technique chosen from extruding, pelletizing, grinding, and molding. In other embodiments, mixing can be performed by at least one of melting, dissolution in a solvent, and dry mixing.

The incorporation of components for the stabilizer composition and optional further additives into the polymer composition is carried out by any suitable method known to those of skill in the art, for example before or after molding or also by applying the dissolved or dispersed stabilizer mixture to the polyolefin, with or without subsequent evaporation of the solvent. The stabilizer components and optional further additives can also be added to the polymer compositions to be stabilized in the form of a masterbatch.

Components of the stabilizer composition and optional further additives can also be added before or during the polymerization or before crosslinking. They can also be incorporated into the polymer composition to be stabilized in pure form (i.e., neat and directly to the resin) or encapsulated in waxes, oils or polymers. Various additives can also be preblended (i.e., mixed together) for simple addition to the polymer compositions to be stabilized. Components of the stabilizer composition and optional further additives can also be sprayed onto the polymer compositions to be stabilized. They are able to dilute other additives (for example the conventional additives indicated above) or their melts so that they can be sprayed also together with these additives onto the polymer compositions to be stabilized. In the case of spherically polymerized polymers it may, for example, be advantageous to apply components of the stabilizer composition optionally together with other additives, by spraying.

It is also contemplated that the components of the stabilizer compositions and/or polymer compositions described herein may be contained in a kit. The kit may include single or multiple components of at least one stabilizer composition according to the invention, at least one polymer composition according to the invention, and at least one further optional additive, each packaged or formulated individually, or single or multiple components of at least one stabilizer composition according to the invention, at least one polymer composition according to the invention, and at least one further optional additive packaged or formulated in combination. Thus, one or more components of a stabilizer composition can be present in first container, and the kit can optionally include one or more components of the stabilizer composition and/or polymer composition in a second or further container. The container or containers are placed within a package, and the package can optionally include administration or mixing instructions in the form of a label or website address on the package, or in the form of an insert included in the packaging of the kit. A kit can include additional components or other means for administering or mixing the components as well as solvents or other means for formulation.

Other Embodiments

1. A process for reducing cycle time in a rotational molding process for producing a polymeric hollow article, the process comprising:
    subjecting a polymer composition and a polymer-stabilizing amount of a stabilizer composition to a rotational molding process, wherein the stabilizer composition comprises:
    i) at least one chroman-based compound according to Formula V

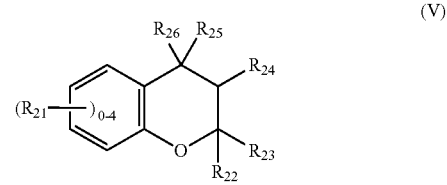

wherein
    $R_{21}$ is present at from 0 to 4 positions of the aromatic portion of Formula V and in each instance is independently chosen from:
        $C_1$-$C_{12}$ hydrocarbyl;
        NR'R", wherein each of R' and R" is independently chosen from H or $C_1$-$C_{12}$ hydrocarbyl; or
        $OR_{27}$, wherein $R_{27}$ is chosen from: H; $C_1$-$C_{12}$ hydrocarbyl; COR'''; or Si($R_{28}$)$_3$, wherein R''' is chosen from H or $C_1$-$C_{20}$ hydrocarbyl; and wherein $R_{28}$ is chosen from $C_1$-$C_{12}$ hydrocarbyl or alkoxy;
    $R_{22}$ is chosen from: H; or $C_1$-$C_{12}$ hydrocarbyl;
    $R_{23}$ is chosen from H; or $C_1$-$C_{20}$ hydrocarbyl;
    each of $R_{24}$-$R_{25}$ is independently chosen from: H; $C_1$-$C_{12}$ hydrocarbyl; or OR"", wherein R"" is chosen from H or $C_1$-$C_{12}$ hydrocarbyl; and
    $R_{26}$ is H, or a bond which together with $R_{25}$ forms =O.

2. A process according to embodiment 1, wherein the cycle time is reduced by at least 4 to 50%.

3. A process for producing a polymeric hollow article, the process comprising:
    a) filling a mold with a polymer composition and a polymer-stabilizing amount of a stabilizer composition, wherein the stabilizer composition comprises:
    at least one chroman-based compound according to Formula V

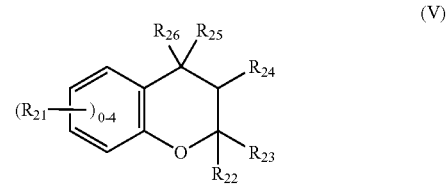

wherein

R$_{21}$ is present at from 0 to 4 positions of the aromatic portion of Formula V and in each instance is independently chosen from:

C$_1$-C$_{12}$ hydrocarbyl;

NR'R", wherein each of R' and R" is independently chosen from H or C$_1$-C$_{12}$ hydrocarbyl; or OR$_{27}$, wherein R$_{27}$ is chosen from: H; C$_1$-C$_{12}$ hydrocarbyl; COR'''; or Si(R$_{28}$)$_3$, wherein R''' is chosen from H or C$_1$-C$_{20}$ hydrocarbyl; and wherein R$_{28}$ is chosen from C$_1$-C$_{12}$ hydrocarbyl or alkoxy;

R$_{22}$ is chosen from: H; or C$_1$-C$_{12}$ hydrocarbyl;

R$_{23}$ is chosen from H; or C$_1$-C$_{20}$ hydrocarbyl;

each of R$_{24}$-R$_{25}$ is independently chosen from: H; C$_1$-C$_{12}$ hydrocarbyl; or OR"", wherein R"" is chosen from H or C$_1$-C$_{12}$ hydrocarbyl; and R$_{26}$ is H, or a bond which together with R$_{25}$ forms =O;

b) rotating the mold around at least 1 axis while heating the mold in an oven, thereby fusing the composition and spreading it to the walls of the mold;

c) cooling the mold; and d) opening the mold to remove the resulting product, thereby producing a polymeric hollow article.

4. A process according to embodiment 3, wherein the temperature of the oven ranges from 70° C. up to 400° C.

5. A process according to any of the preceding embodiments, wherein the stabilizer composition further comprises at least one compound chosen from the group of organic phosphites or phosphonites.

6. A process according to embodiment 5, wherein the at least one organic phosphite or phosphonite is chosen from i) a compound according to Formulas 1-7:

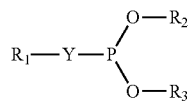 (1)

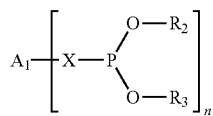 (2)

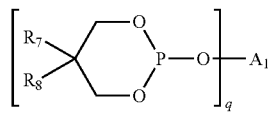 (3)

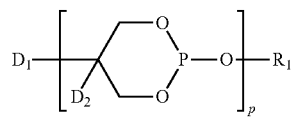 (4)

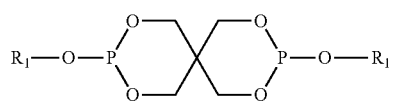 (5)

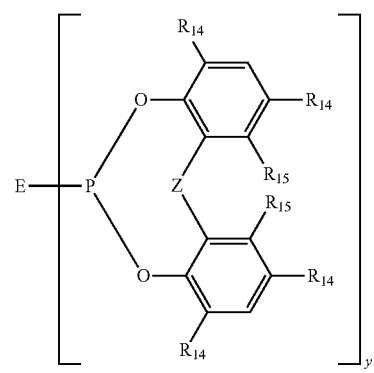 (6)

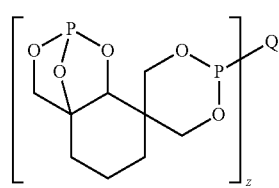 (7)

in which the indices are integral and
n is 2, 3 or 4; p is 1 or 2; q is 2 or 3; r is 4 to 12; y is 1, 2 or 3; and z is 1 to 6;

A$_1$, if n is 2, is C$_2$-C$_{18}$ alkylene; C$_2$-C$_{12}$ alkylene interrupted by oxygen, sulfur or —NR$_4$—; a radical of the formula

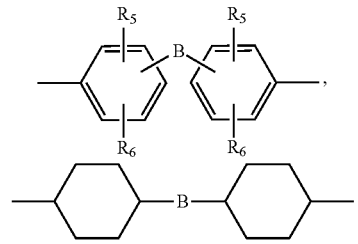

or phenylene;

A$_1$, if n is 3, is a radical of the formula —C$_r$H$_{2r-1}$—;

A$_1$, if n is 4, is

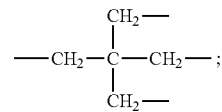

B is a direct bond, —CH$_2$—, —CHR$_4$—, —CR$_1$R$_4$—, sulfur, C$_5$-C$_7$ cycloalkylidene, or cyclohexylidene which is substituted by from 1 to 4 C$_1$-C$_4$ alkyl radicals in position 3, 4 and/or 5;

D$_1$, if p is 1, is C$_1$-C$_4$ alkyl and, if p is 2, is —CH$_2$OCH$_2$—;

D$_2$ is C$_1$-C$_4$ alkyl;

E, if y is 1, is C$_1$-C$_{18}$ alkyl, —OR$_1$ or halogen;

E, if y is 2, is —O-A$_2$-O—, A$_2$ is as defined for A$_1$ when n is 2;

E, if y is 3, is a radical of the formula R$_4$C(CH$_2$O—)$_3$ or N(CH$_2$CH$_2$O—)$_3$;

Q is the radical of an at least z-valent mono or poly alcohol or phenol, this radical being attached via the oxygen atom of the OH group of the mono or poly alcohol or phenol to the phosphorus atom;

$R_1$, $R_2$ and $R_3$ independently of one another are $C_1$-$C_{18}$ alkyl which is unsubstituted or substituted by halogen, —COOR$_4$, —CN or —CONR$_4$R$_4$; $C_2$-$C_{18}$ alkyl interrupted by oxygen, sulfur or —NR$_4$—; $C_7$-$C_9$ phenylalkyl; $C_5$-$C_{12}$ cycloalkyl, phenyl or naphthyl; naphthyl or phenyl substituted by halogen, 1 to 3 alkyl radicals or alkoxy radicals having a total of 1 to 18 carbon atoms or by $C_7$-$C_9$ phenylalkyl; or a radical of the formula

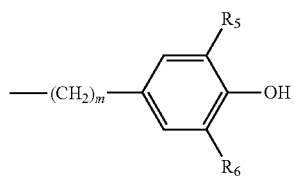

in which m is an integer from the range 3 to 6;
$R_4$ is hydrogen, $C_1$-$C_8$ alkyl, $C_5$-$C_{12}$ cycloalkyl or $C_7$-$C_9$ phenylalkyl,
$R_5$ and $R_6$ independently of one another are hydrogen, $C_1$-$C_5$ alkyl or $C_5$-$C_6$ cycloalkyl,
$R_7$ and $R_8$, if q is 2, independently of one another are $C_1$-$C_4$ alkyl or together are a 2,3-dehydropentamethylene radical; and
$R_7$ and $R_8$, if q is 3, are methyl;
each instance of $R_{14}$ is independently chosen from hydrogen, $C_1$-$C_9$ alkyl or cyclohexyl,
each instance of $R_{15}$ is independently chosen from hydrogen or methyl,
X and Y are each a direct bond or oxygen,
Z is a direct bond, methylene, —C($R_{16}$)$_2$— or sulfur, and
$R_{16}$ is $C_1$-$C_8$ alkyl; or
ii) a trisarylphosphite according to Formula 8:

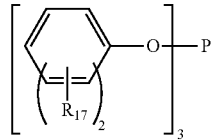

wherein $R_{17}$ is present at from 0 to 5 positions of the aromatic portion of Formula 8 and in each instance is independently chosen from $C_1$-$C_{20}$ alkyl, $C_3$-$C_{20}$ cycloalkyl, $C_4$-$C_{20}$ alkyl cycloalkyl, $C_6$-$C_{10}$ aryl, or $C_7$-$C_{20}$ alkylaryl; or
iii) combinations of i) and ii).

7. A process according to embodiment 6, wherein the organic phosphite or phosphonite is selected from the group consisting of: triphenyl phosphite; diphenyl alkyl phosphites; phenyl dialkyl phosphites; trilauryl phosphite; trioctadecyl phosphite; distearyl pentaerythritol phosphite; tris(2, 4-di-tert-butylphenyl) phosphite; tris(nonylphenyl) phosphite; a compound of formulae (A), (B), (C), (D), (E), (F), (G), (H), (J), (K) and (L):

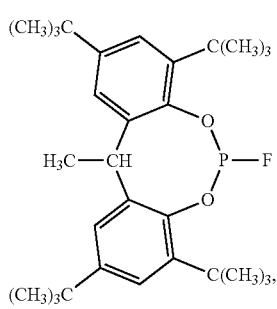

(A)

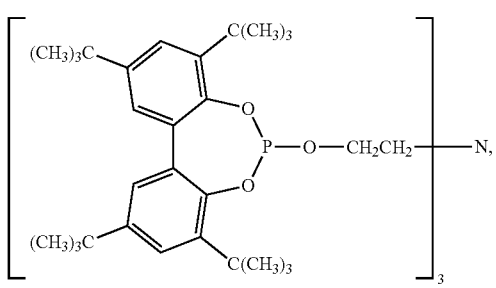

(B)

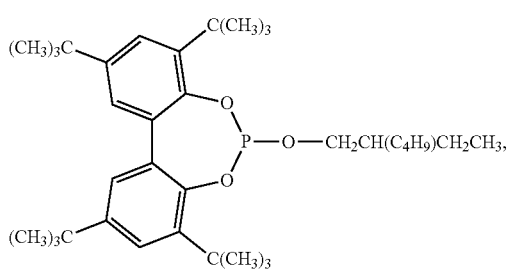

(C)

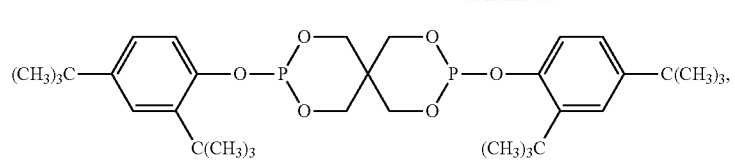
(D)
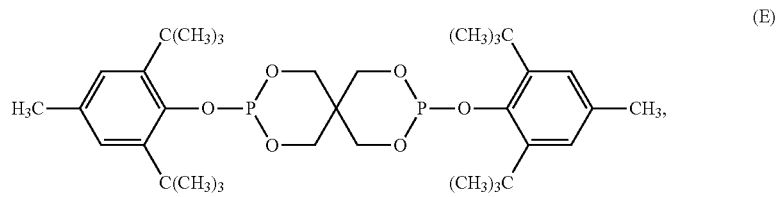
(E)
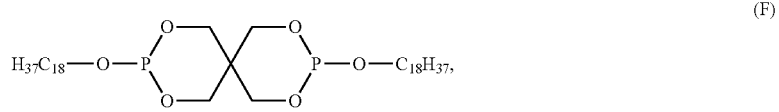
(F)
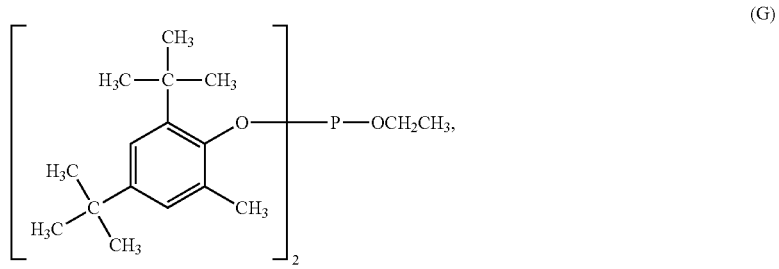
(G)
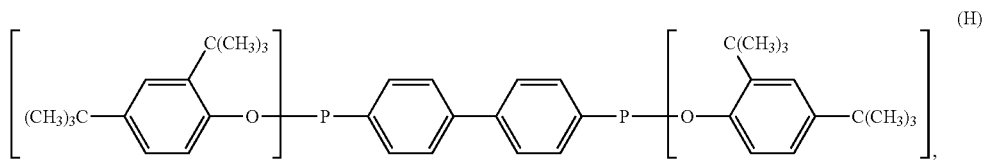
(H)
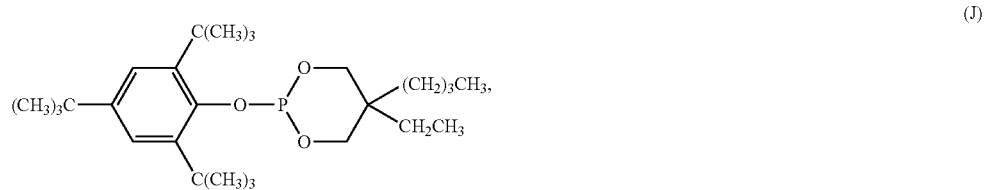
(J)
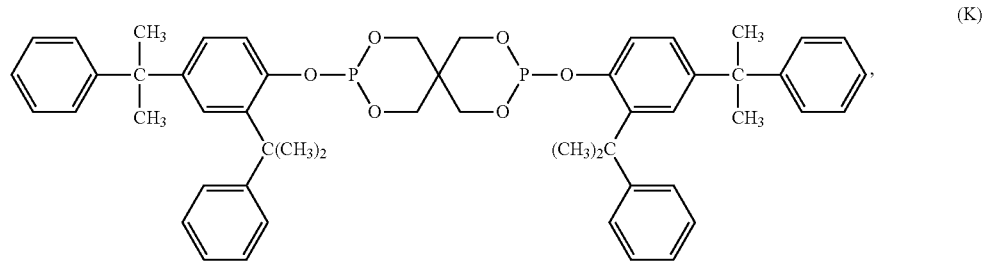
(K)
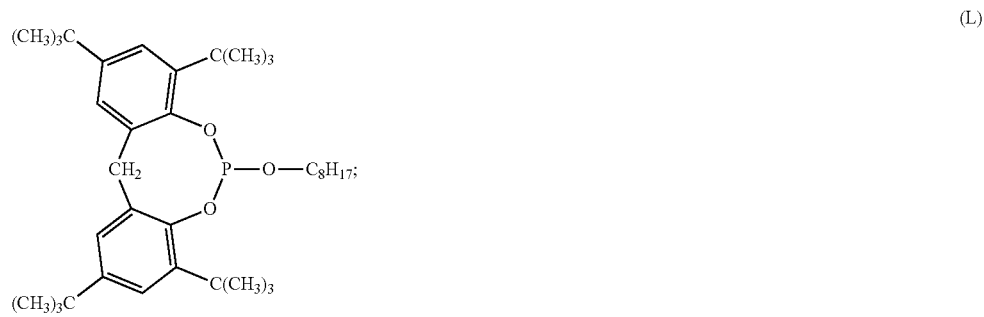
(L)

2-butyl-2-ethyl-1,3-propanediol 2,4,6-tri-t-butylphenol phosphite; bis-(2,6-di-t-butyl-4-methylphenyl) pentaerythritol diphosphite; 2-butyl-2-ethyl-1,3-propanediol 2,4-dicumylphenol phosphite; 2-butyl-2-ethyl-1,3-propanediol 4-methyl-2,6-di-t-butylphenol phosphite; bis-(2,4,6-tri-t-butyl-phenyl) pentaerythritol diphosphite; and combinations thereof.

8. A process according to any one of embodiments 5-7, wherein the at least one organic phosphite or phosphonite is chosen from tris(2,4-di-tert-butylphenyl)phosphite (IRGAFOS®168); Bis(2,4-dicumylphenyl)pentaerythritol diphosphite (DOVERPHOS® S9228); or tetrakis(2,4-di-tert-butylphenyl)4,4'-biphenylene-diphosphonite (IRGAFOS® P-EPQ).

9. A process according to any one of the preceding embodiments, wherein the stabilizer composition further comprises at least one hindered phenol compound.

10. A process according to embodiment 9, wherein the at least one hindered phenol compound comprises a molecular fragment according to one or more of Formula (IVa), (IVb), or (IVc):

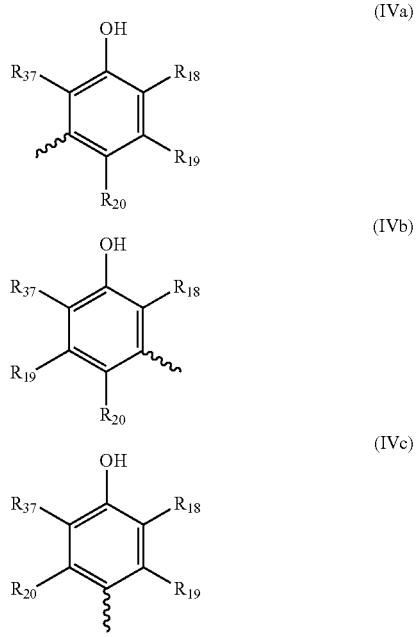

wherein
$R_{18}$ of Formula (IVa), (IVb), and (IVc) is chosen from hydrogen or a $C_{1-4}$ hydrocarbyl;
$R_{19}$ and $R_{20}$ of Formula (IVa), (IVb), and (IVc) are each individually chosen from hydrogen or a $C_1$-$C_{20}$ hydrocarbyl; and
$R_{37}$ of Formula (IVa), (IVb), and (IVc) is chosen from $C_1$-$C_{12}$ hydrocarbyl.

11. A process according to embodiment 10, wherein $R_{18}$ and $R_{37}$ are chosen from methyl or t-butyl.

12. A process according to any one of embodiments 9-11, wherein the at least one hindered phenol compound is selected from the group consisting of: (1,3,5-Tris(4-t-butyl-3-hydroxy-2,6-dimethylbenzyl)-1,3,5-triazine-2,4,6-(1H,3H,5H)-trione; 1,3,5-tris(3,5-di-tert-butyl-4-hydroxybenzyl)-1,3,5-triazine-2,4,6(1H,3H,5H)-trione; 1,1,3-Tris(2'-methyl-4'-hydroxy-5'-t-butylphenyl)butane; Triethylene glycol bis[3-(3-t-butyl-4-hydroxy-5-methylphenyl)propionate]; 4,4'-Thiobis(2-t-butyl-5-methylphenol); 2,2'-Thiodiethylene bis[3-(3-t-butyl-4-hydroxyl-5-methylphenyl)propionate]; Octadecyl 3-(3'-t-butyl-4'-hydroxy-5'-methylphenyl)propionate; Tetrakismethylene(3-t-butyl-4-hydroxy-5-methylhydrocinnamate)methane; N,N'-Hexamethylene bis[3-(3-t-butyl-4-hydroxy-5-methylphenyl)propionamide]; Di(4-tertiarybutyl-3-hydroxy-2,6-dimethyl benzyl) thiodipropionate; and octadecyl 3,5-di-(tert)-butyl-4-hydroxyhydrocinnamate.

13. A process according to any of the preceding embodiments, wherein $R_{21}$ is present in at least one instance as $OR_{27}$.

14. A process according to embodiment 13, wherein $R_{21}$ is present in at least three instances and is chosen from $OR_{27}$ or methyl.

15. A process according to any of the preceding embodiments, wherein $R_{23}$ is a $C_1$-$C_{18}$ hydrocarbyl.

16. A process according to any of the preceding embodiments, wherein the chroman-based compound according to Formula V is a tocopherol.

17. A process according to any of the preceding embodiments, wherein the chroman-based compound is vitamin E or its acetate according to Formula Va

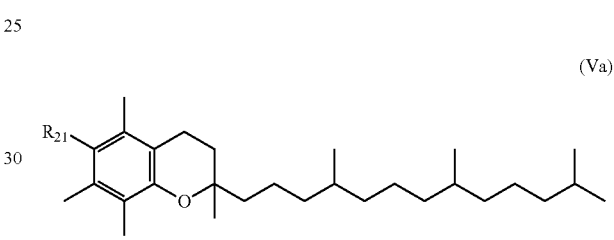

wherein $R_{21}$ is chosen from OH; or —OC(O)CH$_3$, respectively.

18. A process according to any of the preceding embodiments, wherein the chroman-based compound is a blend of compounds according to Formula V.

19. A process according to any of the preceding embodiments, wherein the chroman-based compound is present from 0.001% to 5.0% by weight of the total weight of the stabilizer composition.

20. A process according to embodiment 19, wherein the chroman-based compound is present from 0.01% to 1.0% by weight of the total weight of the stabilizer composition.

21. A process according to any of the preceding embodiments, wherein the polymer composition comprises a polyolefin selected from the group consisting of: i) polymers of monoolefins and diolefins chosen from polypropylene, polyisobutylene, polybut-1-ene, poly-4-methylpent-1-ene, polyisoprene, and polybutadiene; ii) polymers of cycloolefins chosen from cyclopentene, and norbornene; iii) polyethylene chosen from optionally crosslinked polyethylene, high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), very low density polyethylene (VLDPE), and ultralow density polyethylene (ULDPE); iv) copolymers of monoolefins or diolefins with each other or with other vinyl monomers; and v) mixtures of any of i)-iv).

22. A process according to any of the preceding embodiments, wherein the polymer composition further comprises a light stabilizer chosen from: hindered amine light stabilizers, hindered hydroxyl benzoates, nickel phenolates, ultraviolet light stabilizers, or combinations thereof in an amount effective to stabilize the polymer composition against the degradative effects of visible and/or ultraviolet light radiation.

23. A process according to embodiment 22, wherein the light stabilizer is a hindered amine light stabilizer compound comprising a molecular fragment according to Formula (VI):

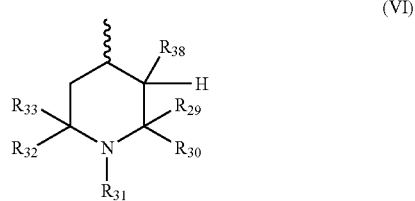

(VI)

wherein
$R_{31}$ is chosen from: hydrogen; OH; $C_1$-$C_{20}$ hydrocarbyl; —$CH_2CN$; $C_1$-$C_{12}$ acyl; or $C_1$-$C_{18}$ alkoxy;
$R_{38}$ is chosen from: hydrogen; or $C_1$-$C_8$ hydrocarbyl; and each of $R_{29}$, $R_{30}$, $R_{32}$, and $R_{33}$ is independently chosen from $C_1$-$C_{20}$ hydrocarbyl, or $R_{29}$ and $R_{30}$ and/or $R_{32}$ and $R_{33}$ taken together with the carbon to which they are attached form a $C_5$-$C_{10}$ cycloalkyl;
or according to Formula (VIa)

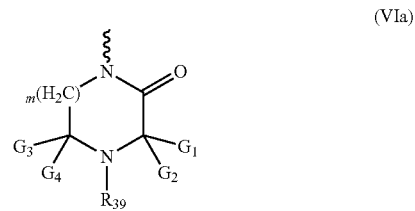

(VIa)

wherein
m is an integer from 1 to 2;
$R_{39}$ is chosen from: hydrogen; OH; $C_1$-$C_{20}$ hydrocarbyl; —$CH_2CN$; $C_1$-$C_{12}$ acyl; or $C_1$-$C_{18}$ alkoxy; and each of $G_1$-$G_4$ is independently chosen from $C_1$-$C_{20}$ hydrocarbyl.

24. A process according to embodiment 22 or embodiment 23, wherein the hindered amine light stabilizer is selected from the group consisting of: bis(2,2,6,6-tetramethylpiperidin-4-yl) sebacate; bis(2,2,6,6-tetramethylpiperidin-4-yl) succinate; bis(1,2,2,6,6-pentamethylpiperidin-4-yl)sebacate; bis(1-octyloxy-2,2,6,6-tetramethylpiperidin-4-yl) sebacate; bis(1,2,2,6,6-pentamethylpiperidin-4-yl) n-butyl 3,5-di-tert-butyl-4-hydroxybenzylmalonate; a condensate of 1-(2-hydroxyethyl)-2,2,6,6-tetramethyl-4-hydroxypiperidine and succinic acid; 2,2,6,6-tetramethylpiperidin-4-yl stearate; 2,2,6,6-tetramethylpiperidin-4-yl dodecanate; 1,2,2,6,6-pentamethylpiperidin-4-yl stearate; 1,2,2,6,6-pentamethylpiperidin-4-yl dodecanate; a condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; a condensate of N,N'-bis(2,2,6,6-tetramethylpiperidin-4-yl)hexamethylenediamine and 4-morpholino-2,6-dichloro-1,3,5-triazine; a condensate of 2-chloro-4,6-bis(4-n-butylamino-2,2,6,6-tetramethylpiperidyl)-1,3,5-triazine and 1,2-bis(3-aminopropylamino)ethane; a condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; a condensate of N,N'-bis(2,2,6,6-tetramethylpiperidin-4-yl)hexamethylenediamine and 4-cyclohexylamino-2,6-dichloro-1,3,5-triazine; a condensate of 1,2-bis(3-aminopropylamino)ethane, 2,4,6-trichloro-1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines; a reaction product of 7,7,9,9-tetramethyl-2-cycloundecyl-1-oxa-3,8-diaza-4-oxospiro [4.5]decane and epichlorohydrin; tetrakis(2,2,6,6-tetramethyl-4-piperidyl) butane-1,2,3,4-tetracarboxylate; 1,2,3,4-butanetetracarboxylic acid, tetrakis(1,2,2,6,6-pentamethyl-4-piperidinyl)ester; 1,2,3,4-butanetetracarboxylic acid, 1,2,2,6,6-pentamethyl-4-piperdinyl tridecyl ester; 1,2,3,4-butanetetracarboxylic acid, 2,2,6,6-tetramethyl-4-piperidinyl tridecyl ester; 1,2,3,4-butanetetracarboxylic acid, polymer with 2,2,6,6-tetramethyl-2,4,8,10-tetraoxaspiro[5.5]-undecane-3,9-diethanol,1,2,2,6,6-pentamethyl-4-piperdinyl ester; 1,2,3,4-butanetetracarboxylic acid, polymer with 2,2,6,6-tetramethyl-2,4,8,10-tetraoxaspiro[5.5]-undecane-3,9-diethanol, 2,2,6,6-tetramethyl-4-piperdinyl ester; bis(1-undecanoxy-2,2,6,6-tetramethylpiperidin-4-yl) carbonate; 1-(2-hydroxy-2-methylpropoxy)-2,2,6,6-tetramethyl-4-piperidinol; 1-(2-hydroxy-2-methylpropoxy)-4-octadecanoyloxy-2,2,6,6-tetramethylpiperidine; 1-(4-octadecanoyloxy-2,2,6,6-tetramethylpiperidin-1-yloxy)-2-octadecanoyloxy-2-methylpropane; 1-(2-hydroxyethyl)-2,2,6,6-tetramethyl-4-piperidinol; a reaction product of 1-(2-hydroxyethyl)-2,2,6,6-tetramethyl-4-piperidinol and dimethylsuccinate; 2,2,4,4-tetramethyl-7-oxa-3,20-diazadispiro[5.1.11.2]heneicosan-21-one; the ester of 2,2,6,6-tetramethyl-4-piperidinol with higher fatty acids; 3-dodecyl-1-(2,2,6,6-tetramethyl-4-piperidyl)pyrrolidine-2,5-dione; 1H-Pyrrole-2,5-dione, 1-octadecyl-, polymer with (1-methylethenyl)benzene and 1-(2,2,6,6-tetramethyl-4-piperidinyl)-1H-pyrrole-2,5-dione; piperazinone, 1,1',1"-[1,3,5-triazine-2,4,6-triyltris[(cyclohexylimino)-2,1-ethanediyl]] tris[3,3,5,5-tetramethyl-; piperazinone, 1,1',1"-[1,3,5-triazine-2,4,6-triyltris[(cyclohexylimino)-2,1-ethanediyl]] tris[3,3,4,5,5-pentamethyl-; the reaction product of 7,7,9,9-tetramethyl-2-cycloundecyl-1-oxa-3,8-diaza-4-oxospiro [4.5]decane and epichlorohydrin; the condensate of N,N'-bis(2,2,6,6-tetramethylpiperidin-4-yl) hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6- bis(4-n-butylamino-1,2,2,6,6-pentamethylpiperidyl)-1,3,5-triazine and 1,2-bis-(3-aminopropylamino)ethane; 2-[(2-hydroxyethyl)amino]-4,6-bis[N-(1-cyclohexyloxy-2,2,6,6-tetramethylpiperidin-4-yl)butylamino-1,3,5-triazine; propanedioic acid, [(4-methoxyphenyl)-methylene]-bis-(1,2,2,6,6-pentamethyl-4-piperidinyl) ester; tetrakis(2,2,6,6-tetramethylpiperidin-4-yl)-1,2,3,4-butanetetracarboxylate; benzenepropanoic acid, 3,5-bis(1,1-dimethylethyl)-4-hydroxy-, 1-[2-[3-[3,5-bis(1,1-dimethylethyl)-4-hydroxyphenyl]-1-oxopropoxy]ethyl]-2,2,6,6-tetramethyl-4-piperidinyl ester; N-(1-octyloxy-2,2,6,6-tetramethylpiperidin-4-yl)-N'-dodecyloxalamide; tris(2,2,6,6-tetramethylpiperidin-4-yl) nitrilotriacetate; 1,5-dioxaspiro{5,5}undecane-3,3-dicarboxylic acid, bis(1,2,2,6,6-pentamethyl-4-piperidinyl): 1,5-dioxaspiro{5,5}undecane-3,3-dicarboxylic acid, bis(2,2,6,6-tetramethyl-4-piperidinyl); the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; 1,2,3,4-butanetetracarboxylic acid, 1,2,2,6,6-pentamethyl-4-piperidinyl tridecyl ester; tetrakis(2,2,6,6-tetramethylpiperidin-4-yl)-1,2,3,4-butanetetracarboxylate; 1,2,3,4-butanetetracarboxylic acid, 2,2,6,6-tetramethyl-4-piperidinyl tridecyl ester; tetrakis(1,2,2,6,6-pentamethylpiperidin-4-yl)-1,2,3,4-butanetetracarboxylate; mixture of 2,2,4,4-tetramethyl-21-oxo-7-oxa-3,20-diazaspiro(5.1.11.2)-heneicosane-20-propanoic acid-dodecylester and 2,2,4,4-tetramethyl-21-oxo-7-oxa-3,20-diazaspiro(5.1.11.2)-heneicosane-20-propanoic acid-tetradecylester; 1H,4H,5H,8H-2,3a,4a,6,7a,8a-hexaazacyclopenta[def]fluorene-4,8-dione, hexahydro-2,6-bis(2,2,6,6-tetramethyl-4-piperidinyl)-; polymethyl[propyl-3-oxy(2',2',6',6'-tetramethyl-4,4'-piperidinyl)]siloxane; polymethyl[propyl-3-oxy(1',2',2',6',6'-pentamethyl-4,4'-piperidinyl)]siloxane; copolymer of methylmethacrylate with ethyl acrylate and 2,2,6,6-tetramethylpiperidin-4-yl acrylate; copolymer of mixed $C_{20}$ to $C_{24}$ alpha-olefins and (2,2,6,6-tetramethylpiperidin-4-yl)succinimide; 1,2,3,4-butanetetracarboxylic acid, polymer with β,β,β',β'-tetramethyl-2,4,8,10-tetraoxaspiro[5.5]undecane-3,9-diethanol, 1,2,2,6,6-pentamethyl-4-piperidinyl ester; 1,2,3,4-butanetetracarboxylic acid, polymer with β,β,β',β'-tetramethyl-2,4,8,10-tetraoxaspiro[5.5]undecane-3,9-diethanol, 2,2,6,6-tetramethyl-4-piperidinyl ester copolymer; 1,3-benzenedicarboxamide, N,N'-bis(2,2,6,6-tetramethyl-4-piperidinyl; 1,1'-(1,10-dioxo-1,10-decanediyl)-bis(hexahydro-2,2,4,4,6-pentamethylpyrimidine; ethane diamide, N-(1-acetyl-2,2,6,6-tetramethylpiperidinyl)-N'-dodecyl; formamide, N,N'-1,6-hexanediylbis[N-(2,2,6,6-tetramethyl-4-piperidinyl); D-glucitol, 1,3:2,4-bis-O-(2,2,6,6-tetramethyl-4-piperidinylidene)-; 2,2,4,4-tetramethyl-7-oxa-3,20-diaza-21-oxo-dispiro[5.1.11.2]heneicosane; propanamide, 2-methyl-N-(2,2,6,6-tetramethyl-4-piperidinyl)-2-[(2,2,6,6-tetramethyl-4-piperidinyl)amino]-; 7-oxa-3,20-diazadispiro[5.1.11.2]heneicosane-20-propanoic acid, 2,2,4,4-tetramethyl-21-oxo-, dodecyl ester; N-(2,2,6,6-tetramethylpiperidin-4-yl)-β-aminopropionic acid dodecyl ester; N-(2,2,6,6-tetramethylpiperidin-4-yl)-N'-aminooxalamide; propanamide, N-(2,2,6,6-tetramethyl-4-piperidinyl)-3-[(2,2,6,6-tetramethyl-4-piperidinyl)amino]-; mixture of 4-hexadecyloxy- and 4-stearyloxy-2,2,6,6-tetramethylpiperidine; 3-dodecyl-1-(1,2,2,6,6-pentamethylpiperidin-4-yl)pyrrolidine-2,5-dione; 3-dodecyl-1-(1-ethanoyl-2,2,6,6-pentamethylpiperidin-4-yl)pyrrolidine-2,5-dione; bis(2,2,6,6-tetramethylpiperidin-4-yl)succinate; bis(1,2,2,6,6-pentamethylpiperidin-4-yl) n-butyl 3,5-di-tert-butyl-4-hydroxybenzylmalonate; tris(2,2,6,6-tetramethylpiperidin-4-yl) nitrilotriacetate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; 2-undecyl-7,7,9,9-tetramethyl-1-oxa-3,8-diaza-4-oxospiro[4.5]decane; 1,5-dioxaspiro{5,5}undecane-3,3-dicarboxylic acid, bis(2,2,6,6-tetramethyl-4-piperidinyl) and 1,5-dioxaspiro{5,5}undecane-3,3-dicarboxylic acid, bis(1,2,2,6,6-pentamethyl-4-piperidinyl); $N^1$-(p-hydroxyethyl)$_{3,3}$-pentamethylene-5,5-dimethylpiperazin-2-one; $N^1$-tert-octyl-3,3,5,5-tetramethyl-diazepin-2-one; $N^1$-tert-octyl-3,3-pentamethylene-5,5-hexamethylene-diazepin-2-one; $N^1$-tert-octyl-3,3-pentamethylene-5,5-dimethylpiperazin-2-one; trans-1,2-cyclohexane-bis-($N^1$-5,5-dimethyl-3,3-pentamethylene-2-piperazinone; trans-1,2-cyclohexane-bis-($N^1$-3,3,5,5-dispiropentamethylene-2-piperazinone); $N^1$-isopropyl-1,4-diazadispiro-(3,3,5,5)pentamethylene-2-piperazinone; $N^1$-isopropyl-1,4-diazadispiro-3,3-pentamethylene-5,5-tetramethylene-2-piperazinone; $N^1$-isopropyl-5,5-dimethyl-3,3-pentamethylene-2-piperazinone; trans-1,2-cyclohexane-bis-$N^1$-(dimethyl-3,3-pentamethylene-2-piperazinone); $N^1$-octyl-5,5-dimethyl-3,3-pentamethylene-1,4-diazepin-2-one; and $N^1$-octyl-1,4-diazadispiro-(3,3,5,5) pentamethylene-1,5-diazepin-2-one.

25. A process according to embodiment 22, wherein the light stabilizer is an ultraviolet light absorber chosen from a 2-hydroxybenzophenone compound, a 2-(2'-hydroxyphenyl)benzotriazole compound, a 2-(2'-hydroxyphenyl)-1,3,5-triazine compound, or combinations thereof.

26. A process according to embodiment 25, wherein the ultraviolet light absorber is a 2-(2'-hydroxyphenyl)-1,3,5-triazine compound according to Formula (VII):

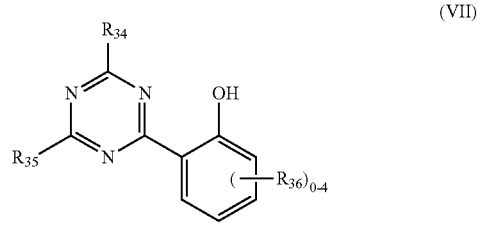

wherein each of $R_{34}$ and $R_{35}$ is independently chosen from $C_6$-$C_{10}$ aryl optionally substituted, $C_1$-$C_{10}$ hydrocarbyl-substituted amino, $C_1$-$C_{10}$ acyl or $C_1$-$C_{10}$ alkoxyl; and wherein $R_{36}$ is present at from 0 to 4 positions of the phenoxy portion of Formula VII and in each instance is independently chosen from hydroxyl, $C_1$-$C_{12}$ hydrocarbyl, $C_1$-$C_{12}$ alkoxyl, $C_1$-$C_{12}$ alkoxyester, or $C_1$-$C_{12}$ acyl.

27. A process according to any one of embodiments 25-26, wherein the 2-(2'-hydroxyphenyl)-1,3,5-triazine compound is selected from the group consisting of: 4,6-bis-(2,4-dimethylphenyl)-2-(2-hydroxy-4-octyloxyphenyl)-s-triazine;

4,6-bis-(2,4-dimethylphenyl)-2-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxy-ethoxy)phenyl]-6-(4-chlorophenyl)-s-triazine; 2,4-bis[2-hydroxy-4-(2-hydroxy-4-(2-hydroxy-ethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine; 2,4-bis(2,4-dihydroxyphenyl)-6-(2,4-dimethylphenyl)-s-triazine; 2,4-bis(4-biphenylyl)-6-[2-hydroxy-4-[(octyloxycarbonyl)ethylideneoxy]phenyl]-s-triazine; 2,4-bis(4-biphenylyl)-6-[2-hydroxy-4-(2-ethylhexyloxy)phenyl]-s-triazine; 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)phenyl]-s-triazine; 2,4-bis(2,4-dimethylphenyl)-6-[2-hydroxy-4(-3-benzyloxy-2-hydroxypropyloxy)phenyl]-s-triazine; 2,4-bis(2-hydroxy-4-n-butyloxyphenyl)-6-(2,4-di-n-butyloxyphenyl)-s-triazine; 2,4-bis(2,4-dimethylphenyl)-6-[2-hydroxy-4-(3-nonyloxy-2-hydroxypropyloxy)-5-α-cumylphenyl]-s-triazine; methylenebis-{2,4-bis(2,4-dimethylphenyl)-6-[2-hydroxy-4-(3-butyloxy-2-hydroxypropoxy)phenyl]-s-triazine}; methylene bridged dimer mixture bridged in the 3:5', 5:5' and 3:3' positions in a 5:4:1 ratio; 2,4,6-tris(2-hydroxy-4-isooctyloxycarbonyliso-propylideneoxy-phenyl)-s-triazine; 2,4-bis(2,4-dimethylphenyl)-6-(2-hydroxy-4-hexyloxy-5-α-cumylphenyl)-s-triazine; 2-(2,4,6-trimethylphenyl)-4,6-bis[2-hydroxy-4-(3-butyloxy-2-hydroxypropyloxy)phenyl]-s-triazine; 2,4,6-tris[2-hydroxy-4-(3-sec-butyloxy-2-hydroxypropyloxy)-phenyl]-s-triazine; mixture of 4,6-bis-(2,4-dimethylphenyl)-2-(2-hydroxy-4-(3-dodecyloxy-2-hydroxypropoxy)phenyl)-s-triazine and 4,6-bis-(2,4-dimethylphenyl)-2-(2-hydroxy-4-(3-tridecyloxy-2-hydroxypropoxy)phenyl)-s-triazine; 4,6-bis-(2,4-dimethylphenyl)-2-(2-hydroxy-4(3-(2-ethylhexyloxy)-2-hydroxypropoxy)-phenyl)-s-triazine; 4,6-diphenyl-2-(4-hexyloxy-2-hydroxyphenyl)-s-triazine; 2-(4,6-Diphenyl-1,3,5-triazin-2-yl)-5-[2-(2-ethylhexanoyloxy)ethoxy]phenol; 2,4,6-tris(2-hydroxy-4-octyloxyphenyl)-1,3,5-triazine; propanoic acid, 2,2',2"-[1,3,5-triazine-2,4,6-triyltris[(3-hydroxy-4, 1-phenylene)oxy]]tris-1,1',1"-trioctyl ester; propanoic acid, 2-[4-[4,6-bis([1,1'-biphenyl]-4-yl)-1,3,5-triazin-2yl]-3-hydroxyphenoxyl]-isooctyl ester; and combinations thereof.

28. A process according to embodiment 22, wherein the light stabilizer is a hindered amine light stabilizer according to embodiment 23 or embodiment 24, and an ultraviolet light absorber according to any one of embodiments 25-27.

29. A process according to any of the preceding embodiments, wherein the polymer composition further comprises at least one compound chosen from:

i) a hydroxylamine compound according to Formula VIII:

(VIII)

wherein $T_1$ is chosen from $C_1$-$C_{36}$ hydrocarbyl, $C_5$-$C_{12}$ cycloalkyl, or $C_7$-$C_9$ aralkyl, optionally substituted; and $T_2$ is chosen from hydrogen or $T_1$;

ii) a tertiary amine oxide compound according to Formula IX:

(IX)

wherein $W_1$ and $W_2$ are each independently chosen from a $C_6$-$C_{36}$ hydrocarbyl chosen from a straight or branched chain $C_6$-$C_{36}$ alkyl, $C_6$-$C_{12}$ aryl, $C_7$-$C_{36}$ aralkyl, $C_7$-$C_{36}$ alkaryl, $C_5$-$C_{36}$ cycloalkyl, $C_6$-$C_{36}$ alkylcycloalkyl; or $C_6$-$C_{36}$ cycloalkylalkyl;

$W_3$ is chosen from a $C_1$-$C_{36}$ hydrocarbyl chosen from a straight or branched chain $C_1$-$C_{36}$ alkyl, $C_6$-$C_{12}$ aryl, $C_7$-$C_{36}$ aralkyl, $C_7$-$C_{36}$ alkaryl, $C_5$-$C_{36}$ cycloalkyl, $C_6$-$C_{36}$ alkylcycloalkyl; and $C_6$-$C_{36}$ cycloalkylalkyl;

with the proviso that at least one of $W_1$, $W_2$ and $W_3$ contains a R carbon-hydrogen bond; and wherein said alkyl, aralkyl, alkaryl, cycloalkyl, alkylcycloalkyl and cycloalkylalkyl groups of $W_1$, $W_2$, and $W_3$ may be interrupted by from one to sixteen moieties selected from the group consisting of —O—, —S—, —SO—, —SO$_2$—, —COO—, —OCO—, —CO—, —NW$_4$—, —CONW$_4$— and —NW$_4$CO—, or wherein said alkyl, aralkyl, alkaryl, cycloalkyl, alkylcycloalkyl and cycloalkylalkyl groups of $W_1$, $W_2$, and $W_3$ may be substituted with from one to sixteen substituents selected from the group consisting of —OW$_4$, —SW$_4$, —COOW$_4$, —OCOW$_4$, —COW$_4$, —N(W$_4$)$_2$, —CON(W$_4$)$_2$, —NW$_4$COW$_4$ and 5- and 6-membered rings containing the —C(CH$_3$)(CH$_2$R$_x$)NL(CH$_2$R$_x$)(CH$_3$)C— group, wherein $W_4$ is chosen from hydrogen or $C_1$-$C_8$ alkyl;

$R_x$ is chosen from hydrogen or methyl; and

L is chosen from a $C_1$-$C_{30}$ alkyl, a —C(O)R moiety wherein R is a $C_1$-$C_{30}$ straight or branched chain alkyl group, or a —OR moiety wherein R is a $C_1$-$C_{30}$ straight or branched chain alkyl group; or wherein said alkyl, aralkyl, alkaryl, cycloalkyl, alkylcycloalkyl and cycloalkylalkyl groups of $W_1$, $W_2$ and $W_3$ are both interrupted and substituted with any of the moieties and/or substituents mentioned above; and wherein said aryl groups of $W_1$, $W_2$ and $W_3$ may be substituted with from one to three compounds independently chosen from halogen, $C_1$-$C_8$ alkyl, or $C_1$-$C_8$ alkoxy; or iii) combinations of i)-ii).

30. A process according to embodiment 29, wherein the compound according to Formula VIII is a N,N-dihydrocarbylhydroxylamine wherein $T_1$ and $T_2$ are independently chosen from benzyl, ethyl, octyl, lauryl, dodecyl, tetradecyl, hexadecyl, heptadecyl or octadecyl; or wherein $T_1$ and $T_2$ are each the alkyl mixture found in hydrogenated tallow amine.

31. A process according to embodiment 29 or embodiment 30, wherein the compound according to Formula VIII is a N,N-dihydrocarbylhydroxylamine chosen from: N,N-dibenzylhydroxylamine; N,N-diethylhydroxylamine; N,N-dioctylhydroxylamine; N,N-dilaurylhydroxylamine; N,N-didodecylhydroxylamine; N,N-ditetradecylhydroxyaamine; N,N-dihexadecylhydroxylamine; N,N-dioctadecylhydroxylamine; N-hexadecyl-N-tetradecylhydroxylamine; N-hexadecyl-N-heptadecylhydroxylamine; N-hexadecyl-N-octadecylhydroxylamine; N-heptadecyl-N-octadecylhydroxylamine; or N,N-di(hydrogenated tallow) hydroxylamine.

32. A process according to any of the preceding embodiments, wherein the polymer composition further comprises at least one compound chosen from co-additives; nucleating agents; fillers; reinforcing agents; polymer additives; or combinations thereof.

33. A process according to any of the preceding embodiments, wherein the stabilizer composition is present from 0.001% to 65.0% by weight of the total weight of the polymer composition.

34. A process according to embodiment 33, wherein the stabilizer composition is present from 0.01% to 25% by weight of the total weight of the polymer composition.

35. A process according to embodiment 33, wherein the stabilizer composition is present from 0.01% to 10% by weight of the total weight of the polymer composition.

36. A process according to any one of the preceding embodiments further characterized in that the polymer composition remains stable and retains its optimal mechanical and/or physical properties over a longer period of time in the oven.

37. A stabilizer composition comprising:
a) at least one compound chosen from the group of organic phosphites or phosphonites;
b) at least one hindered phenol compound; and
c) from 0.001% to 5% by weight of the total of at least one chroman-based compound according to Formula V:

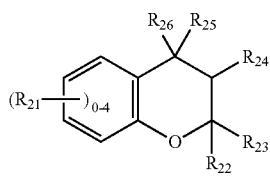

wherein $R_{21}$ is present at from 0 to 4 positions of the aromatic portion of Formula V and in each instance is independently chosen from:

$C_1$-$C_{12}$ hydrocarbyl;

NR'R", wherein each of R' and R" is independently chosen from H or $C_1$-$C_{12}$ hydrocarbyl; or $OR_{27}$, wherein $R_{27}$ is chosen from: H; $C_1$-$C_{12}$ hydrocarbyl; COR'''; or $Si(R_{28})_3$, wherein R''' is chosen from H or $C_1$-$C_{20}$ hydrocarbyl; and wherein $R_{28}$ is chosen from $C_1$-$C_{12}$ hydrocarbyl or alkoxy;

$R_{22}$ is chosen from: H; or $C_1$-$C_{12}$ hydrocarbyl;

$R_{23}$ is chosen from H; or $C_1$-$C_{20}$ hydrocarbyl; and each of $R_{24}$-$R_{25}$ is independently chosen from: H; $C_1$-$C_{12}$ hydrocarbyl; or OR"", wherein R"" is chosen from H or $C_1$-$C_{12}$ hydrocarbyl; and $R_{26}$ is H, or a bond which together with $R_{25}$ forms =O.

38. A stabilizer composition consisting of:
a) at least one compound chosen from the group of organic phosphites or phosphonites;
b) at least one hindered phenol compound; and
c) at least one chroman-based compound according to Formula V:

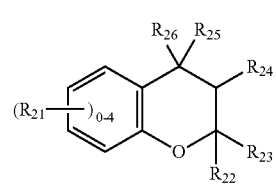

wherein $R_{21}$ is present at from 0 to 4 positions of the aromatic portion of Formula V and in each instance is independently chosen from:

$C_1$-$C_{12}$ hydrocarbyl;

NR'R", wherein each of R' and R" is independently chosen from H or $C_1$-$C_{12}$ hydrocarbyl; or $OR_{27}$, wherein $R_{27}$ is chosen from: H; $C_1$-$C_{12}$ hydrocarbyl; COR'''; or $Si(R_{28})_3$, wherein R''' is chosen from H or $C_1$-$C_{20}$ hydrocarbyl; and wherein $R_{28}$ is chosen from $C_1$-$C_{12}$ hydrocarbyl or alkoxy;

$R_{22}$ is chosen from: H; or $C_1$-$C_{12}$ hydrocarbyl;

$R_{23}$ is chosen from H; or $C_1$-$C_{20}$ hydrocarbyl; and each of $R_{24}$-$R_{25}$ is independently chosen from: H; $C_1$-$C_{12}$ hydrocarbyl; or OR"", wherein R"" is chosen from H or $C_1$-$C_{12}$ hydrocarbyl; and $R_{26}$ is H, or a bond which together with $R_{25}$ forms =O.

39. A stabilizer composition according to embodiment 37 or embodiment 38, wherein $R_{21}$ is present in at least one instance as $OR_{27}$.

40. A stabilizer composition according to any one of embodiments 37 to 39, wherein the chroman-based compound is vitamin E or its acetate according to Formula Va

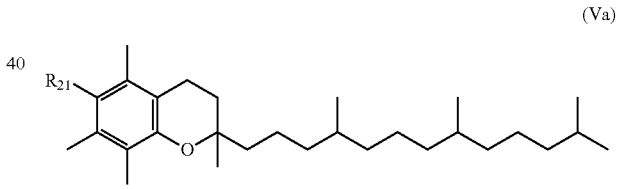

wherein $R_{21}$ is chosen from OH; or —OC(O)CH$_3$, respectively.

41. A kit for stabilizing a polyolefin composition for use in a rotomolding process comprising in one or more containers a polymer-stabilizing amount of a stabilizer composition according to any one of embodiments 37 to 40.

42. A kit according to embodiment 41 further comprising in the same or an additional container one or more additive.

43. A rotomolded article:
a) produced by a process according to any one of embodiments 1-36; or
b) comprising a stabilizer composition according to any one of embodiments 37 to 40.

EXAMPLES

The following examples are provided to assist one skilled in the art to further understand certain embodiments of the present invention. These examples are intended for illustration purposes and are not to be construed as limiting the scope of the various embodiments of the present invention.

Example 1—Preparation of Polyolefin Hollow Articles Using the Rotational Molding Process 50 lb. batches of LLDPE formulated with any type of commercially available stabilizer additive package is dry blended and compounded at 190° C. on a Davis Standard single screw extruder, with a 24:1 L/D screw with a mixing head running at 65 RPM. The resulting pellets are ground to rotomesh powder (less than 35 micron) on a Reduction Engineering pulverizor.

Using enough resin to produce a ⅛"-¼" thick walled part, the formulation is rotationally molded using laboratory scale equipment (e.g., a Ferry E-40 shuttle rotational molder). The ground resin is placed in a cast aluminum mold, which is rotated biaxially in a gas fired oven heated to a temperature of 630° F. (332° C.). The arm ratio for the cast aluminum mold is 8:2. After rotating in the oven for specific time intervals, the mold is removed from the oven and air cooled for 13 minutes while still rotating, followed by a 2 minute water spray, and then 1 minute in circulating air. After the cooling cycle, the mold is opened and the hollow part is removed and then tested by measuring the mean failure energy (MFE) of the part. Sections can be cut from the part and then tested according to the "Dart Drop Low Temperature Impact Resistance Test Procedure," per American Rotational Molders (ARM).

Formulations that achieve the highest mean fracture energy (MFE) at the shortest rotational molding time interval are desirable (reduced cycle time), as well as formulations that show retention of high MFE at longer cycle times (broad process window).

The color (or yellowness) of the molded part can also be tested. Prior to the impact test, the impact specimen from the upper left corner is read for color. The sample is read using a GretagMacbeth Color i7 spectrophotometer. The yellowness according to ASTM D1925 is reported from the mold side of the roto molded part. Positive yellowness values indicates presence and magnitude of yellowness (generally unfavorable), while a negative yellowness value indicates that a material appears bluish (generally favorable).

Example 2—Preparation of Polyolefin Hollow Articles Using the Rotational Molding Process—(Comparative)

Control and test samples are prepared and tested according to Example 1 above. The additive formulation for each sample is provided in Table 1 below.

TABLE 1

| Sample | Additive Formulation |
| --- | --- |
| Control (high phenolic) | 0.075% CYANOX ® 1790 (phenolic) |
| | 0.06% IRGAFOS ® 168 (phosphite) |
| | 0.035% zinc stearate (co-stabilizer) |
| Comparative 1 (invention) | 0.0075% CYANOX ® 1790 (phenolic) |
| | 0.06% IRGAFOS ® 168 (phosphite) |
| | 0.05% vitamin E (chroman-based compound) |
| | 0.035% zinc stearate (co-stabilizer) |
| Comparative 2 (low phenolic) | 0.0075% CYANOX ® 1790 (phenolic) |
| | 0.06% IRGAFOS ® 168 (phosphite) |
| | 0.035% zinc stearate (co-stabilizer) |

In all cases the LLDPE resin contains 0.035% by weight of the total polymer composition of zinc stearate. The samples are rotomolded and tested according to the ARM procedure as described in Example 1. The stabilizer formulations of the present invention provide superior and unexpected properties compared to the state-of-the-art stabilizer formulations used in the rotomolding process. The mean failure energy (MFE) of the sample containing the stabilizer formulation according to the invention reached maximum MFE sooner than either of the control sample containing the typical commercial stabilizer system or the sample containing the low phenolic stabilizer system, and also maintained a higher MFE for a longer period of time than expected (FIG. 1). Accordingly, the rotomolded LLDPE sample containing the stabilizer formulation according to the invention gave superior performance over both the control sample and the low phenolic sample.

Example 3—Preparation of Polyolefin Hollow Articles Using the Rotational Molding Process—(Comparative—Resin 1)

Control and test samples are prepared and tested according to Example 1 above. The LLDPE resin is the same as in Example 2 (Resin 1). The additive formulation for each sample is provided in Table 2 below.

TABLE 2

| Sample | Additive Formulation |
| --- | --- |
| Control | 0.035% IRGANOX ® 3114 (phenolic antioxidant) |
| | 0.11% IRGAFOS ® 168 (phosphite) |
| | 0.035% zinc stearate (co-stabilizer) |
| Invention | 0.06% IRGAFOS ® 168 (phosphite) |
| | 0.05% vitamin E acetate (chroman-based compound) |
| | 0.035% zinc stearate (co-stabilizer) |

Figure 2A:
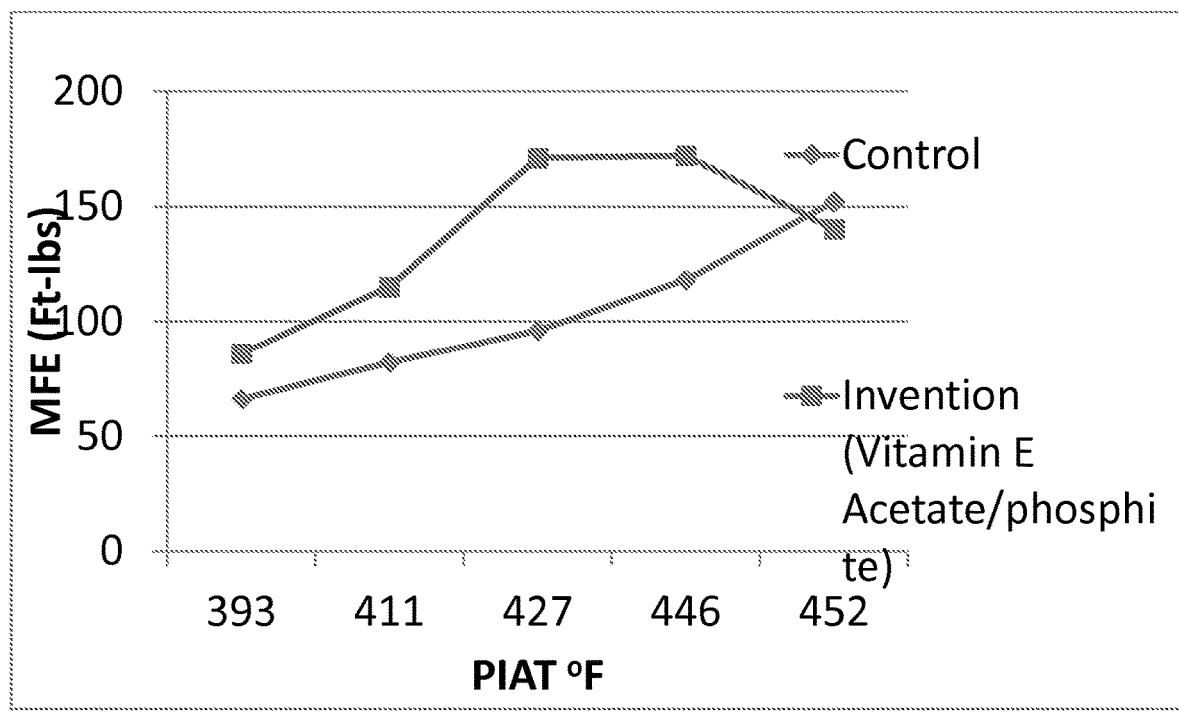
FIGS. 2A-B illustrate the MFE of ¼" rotomolded parts made with control stabilizer (♦) and stabilizer system according to the invention (■) in a LLDPE resin provided by a particular supplier (Resin 1), and the Yellowness Index of the same rotomolded parts as a function of peak internal air temperature.

The samples are rotomolded and tested according to the ARM procedure as described in Example 1, to ¼" thickness. The stabilizer formulations of the present invention provide superior and unexpected properties compared to the state-of-the-art stabilizer formulations used in the rotomolding process. The mean failure energy (MFE) of the sample containing the stabilizer formulation according to the invention reached maximum MFE sooner than the control sample containing the typical commercial stabilizer system or the sample containing the low phenolic stabilizer system, and also maintained a higher MFE for a longer period of time than expected (FIG. 2A). Accordingly, the rotomolded LLDPE sample containing the stabilizer formulation according to the invention gave superior performance over both the control sample and the low phenolic sample.

Figure 2B:
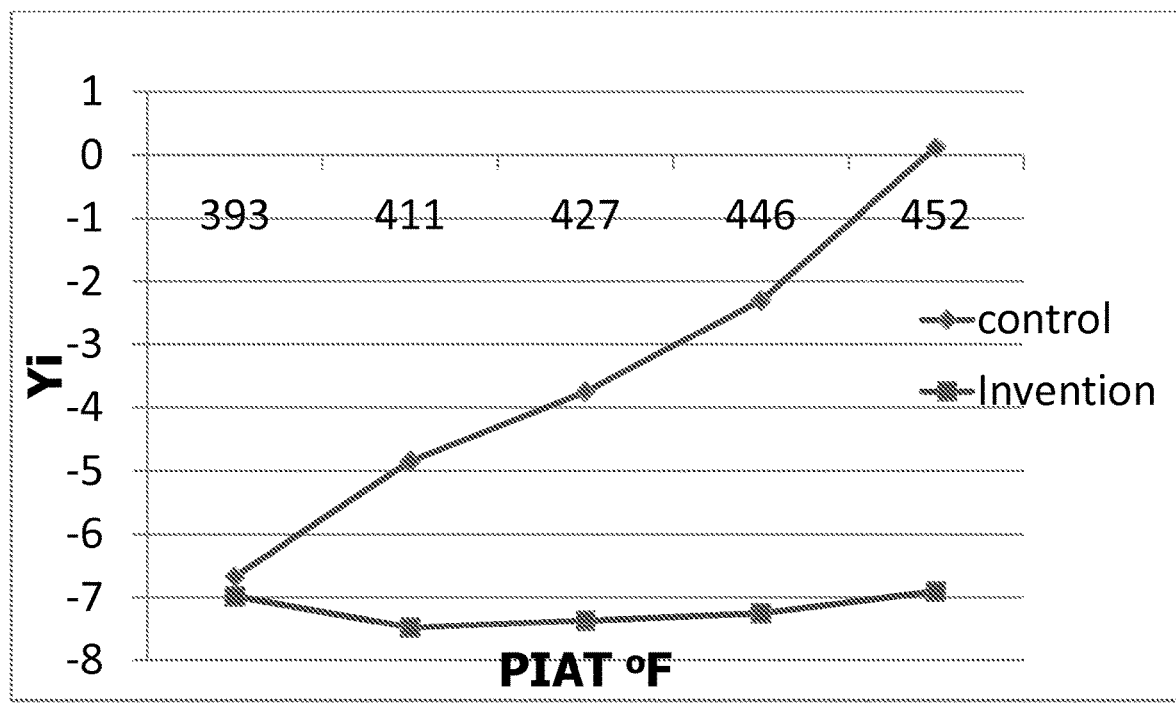

The Yellowness Index is also tested. As seen in FIG. 2B, the Yellowness Index remains relatively flat in the rotomolded part made with the stabilizer system according to the invention even as the peak internal air temperature rises. Conversely, the Yellowness Index rises as the peak internal air temperature rises in the Control sample.

Example 4—Preparation of Polyolefin Hollow Articles Using the Rotational Molding Process—(Comparative—Resin 2)

Control and test samples are prepared and tested according to Example 1 above. However, in this Example the LLDPE resin (Resin 2) is provided by a different supplier than that of Examples 2 and 3. The additive formulation for each sample is provided in Table 3 below.

TABLE 3

| Sample | Additive Formulation |
|---|---|
| Control 1 | 0.035% IRGANOX ® 3114 (phenolic antioxidant) |
| | 0.09% IRGAFOS ® 168 (phosphite) |
| | 0.035% zinc stearate (co-stabilizer) |
| Invention | 0.06% DOVERPHOS ® 9228 (phosphite) |
| | 0.05% vitamin E acetate (chroman-based compound) |
| | 0.05% zinc stearate (co-stabilizer) |
| Control 2 | 0.075% CYANOX ® 2777* (phenolic/phosphite) |
| | 0.35 zinc stearate (co-stabilizer) |

*CYANOX ® 2777 = CYANOX ® 1790 (phenolic) + IRGAFOS ® 168 (phosphite)

Figure 3A:
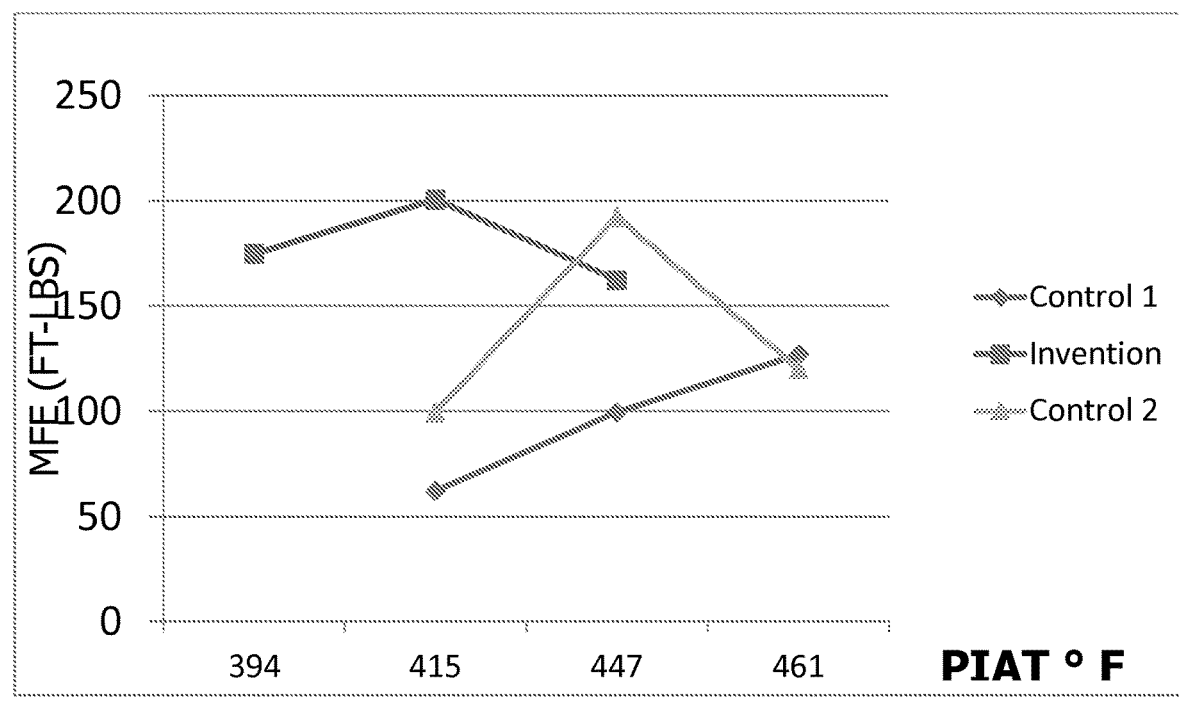
FIGS. 3A-B illustrate the MFE of ¼" rotomolded parts made with control/state-of-the-art stabilizer (♦); stabilizer system according to the invention (■); and a second control/state-of-the-art stabilizer (▲) in a LLDPE resin provided by a different supplier (Resin 2), and the Yellowness Index of the same rotomolded parts as a function of peak internal air temperature.

The samples are rotomolded and tested according to the ARM procedure as described in Example 1, to ¼" thickness. Again, it is seen that the stabilizer formulations of the present invention provide superior and unexpected properties compared to the state-of-the-art stabilizer formulations used in the rotomolding process. The mean failure energy (MFE) of the sample containing the stabilizer formulation according to the invention reached maximum MFE sooner than either of the control sample containing the typical commercial stabilizer system or the sample containing the low phenolic stabilizer system, and also maintained a higher MFE for a longer period of time than expected (FIG. 3A). Accordingly, the rotomolded LLDPE sample containing the stabilizer formulation according to the invention gave superior performance over both the control samples.

Figure 3B:
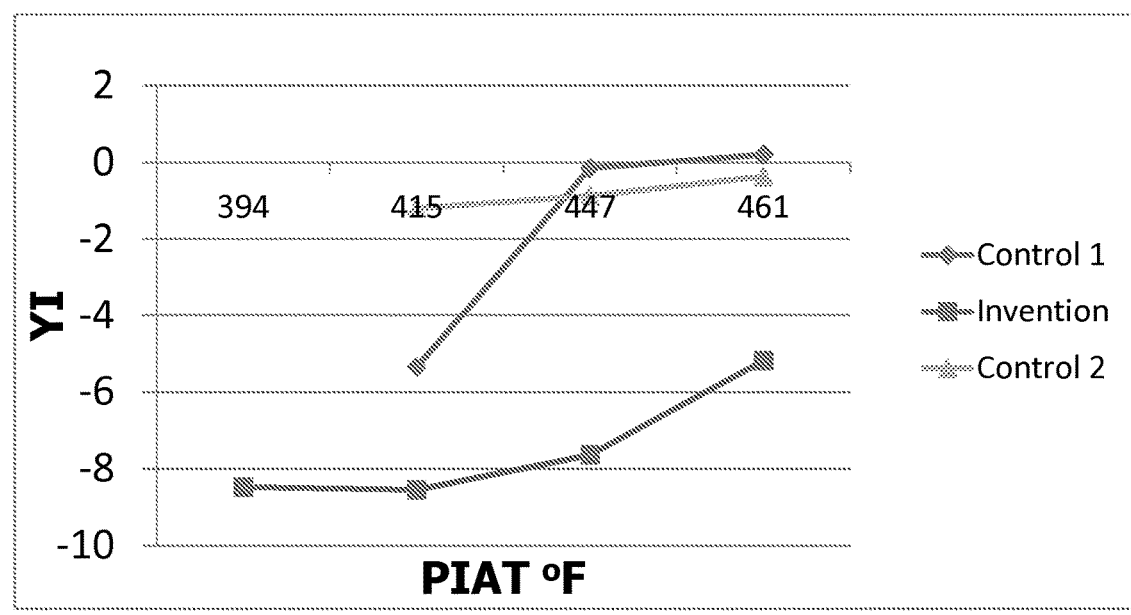

The Yellowness Index is also tested. As seen in FIG. 3B, the Yellowness Index remains lower as the peak internal air temperature rises in the rotomolded part made with the stabilizer system according to the invention than with either of the control samples.

The results demonstrate that the heating times required to achieve optimal cure of a polyolefin article using a standard rotomolding process can be reduced by using the processing stabilizer systems described in detail herein. Reduction of heating times provides the direct benefits of lower energy costs and increased production efficiency without compromising physical and/or mechanical properties of the rotomolded article. The new rotomolding processing stabilizer systems described herein are also shown to provide a broad processing window, thereby enabling the production of parts having high impact strength over a broader range of peak internal air temperatures or heating times versus conventional processing stabilizer systems. Accordingly, these new processing stabilizer systems provide an excellent alternative to other approaches and/or systems to accelerate the sintering/densification of the polymer resin during the rotomolding process.

Various patent and/or scientific literature references have been referred to throughout this application. The disclosures of these publications in their entireties are hereby incorporated by reference as if written herein. In view of the above description and the examples, one of ordinary skill in the art will be able to practice the disclosure as claimed without undue experimentation.

Although the foregoing description has shown, described, and pointed out the fundamental novel features of the present teachings, it will be understood that various omissions, substitutions, and changes in the form of the detail of the apparatus as illustrated, as well as the uses thereof, may be made by those skilled in the art, without departing from the scope of the present teachings. Consequently, the scope of the present teachings should not be limited to the foregoing discussion, but should be defined by the appended claims.

We claim:
1. A process for producing a stabilized polymeric hollow article in a rotational molding operation, the process comprising:
 a) filling a mold with a polyolefin and 0.01 to 10% by weight of the total weight of the polyolefin of a stabilizer composition, wherein said stabilizer composition comprises:
  i) vitamin E acetate;
  ii) a phosphite or phosphonite compound; and
  iii) at least one basic co-additive selected from calcium stearate, zinc stearate, magnesium behenate, magnesium stearate, sodium ricinoleate, or potassium palmitate;
 b) rotating the mold around at least one axis while heating the mold in an oven for a time interval sufficient to achieve sintering and laydown of the polyolefin, thereby spreading the polyolefin to the walls of the mold;
 c) cooling the heated mold; and
 d) opening the mold to remove a resulting product in the form of a stabilized polymeric hollow article;
 wherein the polyolefin comprises linear low density polyethylene (LLDPE), medium density polyethylene (MDPE), high density polyethylene (HDPE), or polypropylene; and
 wherein the polyolefin, phosphite or phosphonite compound, and at least one basic co-additive, and amounts of the vitamin E acetate, phosphite or phosphonite compound, and at least one basic co-additive are selected to reach maximum mean failure energy (MFE) of the article at a shorter time interval of the rotational molding operation, to retain a higher MFE of the article over a longer heating time of the rotational molding operation, and to enlarge a processing window of the rotational molding operation to a peak internal air temperature (PIAT) of up to 452° F. with yellowness index of the article remaining substantially unchanged up to a PIAT of 452° F., even in the absence of a sterically hindered amine light stabilizer (HALS).

2. The process of claim 1, wherein the polyolefin is linear low density polyethylene (LLDPE).

3. The process of claim 1, wherein the phosphite or phosphonite compound is a phosphite compound.

4. The process of claim 3, wherein the phosphite compound is selected from tris(2,4-di-tert-butylphenyl)phosphite and bis(2,4-dicumylphenyl)pentaerythritol diphosphate.

5. The process of claim 1, wherein the at least one basic co-additive is zinc stearate.

6. The process of claim 1, wherein 0.05% by weight of the vitamin E acetate, 0.06% by weight of the phosphite, and either 0.035% or 0.05% by weight of the zinc stearate are present based on the total weight of the polyolefin.

7. The process of claim 1, wherein the article has a ⅛" to ¼" thickness.

8. The process of claim 1, wherein the polyolefin and amounts of the vitamin E acetate, the phosphite or phosphonite compound, and the basic co-additive in the stabilizer composition are further selected to reduce a heating time of the rotational molding operation for achieving optimal cure without compromising physical and/or mechanical properties of the article.

* * * * *